US006521619B2

(12) United States Patent
Link et al.

(10) Patent No.: US 6,521,619 B2
(45) Date of Patent: Feb. 18, 2003

(54) ARYL PHENYLCYCLOPROPYL SULFIDE DERIVATIVES AND THEIR USE AS CELL ADHESION INHIBITING ANTI-INFLAMMATORY AND IMMUNE SUPPRESSIVE AGENTS

(75) Inventors: James T. Link, Evanston, IL (US); Bryan K. Sorensen, Waukegan, IL (US)

(73) Assignees: Icos Corporation, Bothell, WA (US); Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/888,687

(22) Filed: Jun. 25, 2001

(65) Prior Publication Data

US 2002/0156314 A1 Oct. 24, 2002

Related U.S. Application Data

(60) Provisional application No. 60/215,060, filed on Jun. 29, 2000.

(51) Int. Cl.⁷ .................... C07D 295/08; A61K 31/33; A61K 31/11; A61P 37/06; C07C 47/47
(52) U.S. Cl. ................ 514/237.2; 514/232.2; 514/255.01; 514/210.17; 514/330; 514/331; 514/424; 514/560; 514/578; 544/141; 544/159; 544/387; 546/226; 546/234; 548/524; 548/530; 548/953; 560/9; 562/426; 562/431
(58) Field of Search ................ 548/530, 953, 548/524; 546/226, 234; 544/141, 387, 159; 560/9; 562/426; 514/424, 570, 330, 232.2, 331, 237.2, 568, 255.01, 210.17

(56) References Cited

U.S. PATENT DOCUMENTS

| | | | |
|---|---|---|---|
| 4,973,599 A | 11/1990 | Gilman et al. | |
| 5,028,629 A | 7/1991 | Hite et al. | |
| 5,208,253 A | 5/1993 | Boschelli et al. | |
| 5,776,951 A | 7/1998 | Arrowsmith et al. | |
| 5,817,862 A | 10/1998 | Poetsch et al. | |
| 5,883,106 A | 3/1999 | Stevens et al. | |
| 5,883,133 A | 3/1999 | Schwark et al. | |
| 5,912,266 A | 6/1999 | Perez | |
| 6,110,922 A | 8/2000 | Link et al. | |

FOREIGN PATENT DOCUMENTS

| | | |
|---|---|---|
| DE | 2123383 | 12/1971 |
| EP | 0068998 A1 | 6/1982 |
| EP | 0219756 | 10/1986 |
| EP | 0559743 B1 | 11/1991 |
| EP | 835 867 | 4/1998 |
| EP | 887 340 | 12/1998 |
| GB | 2 117 760 A | 10/1993 |
| JP | 12072766 | 3/2000 |
| WO | WO94/27947 | 12/1994 |
| WO | WO 94/27947 | * 12/1994 |
| WO | WO98/13347 | 4/1998 |
| WO | WO98/39303 | 9/1998 |
| WO | WO98/54207 | 12/1998 |
| WO | WO99/11258 | 3/1999 |
| WO | WO99/20617 | 4/1999 |
| WO | WO99/20618 | 4/1999 |
| WO | WO99/47497 | 9/1999 |
| WO | WO99/49856 | 10/1999 |
| WO | WO00/15604 | 3/2000 |
| WO | WO00/15645 | 3/2000 |
| WO | WO00/21920 | 4/2000 |
| WO | WO 01/27102 | 4/2000 |
| WO | WO00/39081 | 7/2000 |
| WO | WO00/60355 | 10/2000 |
| WO | WO01/06984 | 2/2001 |
| WO | WO01/07052 | 2/2001 |

OTHER PUBLICATIONS

Ali, H. et al., *Mechanisms of Inflammation and Leukocyte Activation*, Med. Clin. North America (1997) 81:1–28.
Bella, J., et al. *The Structure of the Two Amino–terminal Domains of Human ICAM–1 Suggests How it Functions as a Rhinovirus Receptor and As An LFA–1 Integrin Ligand*, Proc. Natl. Acad. Sci. USA (1998) 95:4140–4145.
Binnerts, M.E., et al. *How LFA–1 Binds to Different Ligands*, Immunol Today (1999) 20:240–245.
Boschelli, D.H., et al. *Inhibition of E–Selectin–, ICAM–1–, and VCAM–1–Mediated Cell Adhesion by Benzo[b]thiophene–, Benzofuran–, Indole–, and Naphthalene–2–Carboxamides: Indentification of PD 144795 as an Antiinflammatory Agent*, J. Med. Chem. (1995) 38:4597–4614.
Carlos, T.M., *Leukocyte–Endothelial Adhesion Molecules*. Blood (1994) 84:2068–2101.
Edwards, C.P. et al., *Mapping the Intercellular Adhesion Molecule–1 and –2 Binding Site on the Inserted Domain of Leukocyte Function–associated Antigen–1*, J. Biol. Chem. (1998) 273:28937–28944.
Emeigh, J.E., et al., *Small Molecule Antagonists of LFA–1–Mediated Cell Adhesion*. MEDI 256, 221st ACS National Meeting, 2001, San Diego, CA USA.
Fisher, K.L., et al., *Identification of the Binding Site in Intercellular Adhesion Molecule 1 for its Receptor, Leukocyte Function–associated Antigen 1*. (1997) Mol. Biol. Cell 8:501–515.
Gadek, T.R., et al., *Identification and Characterization of Antagonists of the LFA–1/ICAM–1 Protein–Protein Interaction as Novel Immunomodulatory Agents*. 220th ACS National Meeting, Washington, D.C., USA (2000) MEDI 177.

(List continued on next page.)

Primary Examiner—T. A. Solola
Assistant Examiner—Andrea D. Small
(74) Attorney, Agent, or Firm—Sheldon & Mak

(57) ABSTRACT

The present invention relates to novel cyclopropane-containing diaryl sulfide compounds that are useful for treating inflammatory and immune diseases, to pharmaceutical compositions comprising these compounds, and to methods of inhibiting inflammation or suppressing immune response in a mammal.

9 Claims, No Drawings

OTHER PUBLICATIONS

Gahmberg, C.G., *Leukocyte Adhesion: CD11/CD18 Integrins and Intercullular Adhesion Molecules*, Curr. Opin. Cell Biol. (1997) 9:643–650.

Gahmberg, C.G., *Leukocyte Adhesion: Structure and Function of Human Leukocyte $\beta_2$ integrins and Their Cellular Ligands*. (1997) Eur. J. Biochem. 245:215–232.

Green, J.M., *T Cell Receptor Stimulation, But Not CD28 Costimulation, Is Dependent on LFA–1–Mediated Events*, Eur.. J. Immunology (1994) 24:265–272.

Hamilton, G.S., et al., *Fluorenylalkanoic and Benzoic Acids as Novel Inhibitors of Cell Adhesion Processes in Leukocytes*. (1995) 38:1650–1656.

Henricks, P.A., *Pharmacological modulation of cell adhesion molecules*, Eur. J. Pharmacol. (1998) 344:1–13.

Huang, C., *A Binding Interface on the I Domain of Lymphocyte Function–associated Antigen–1 (LFA–1) Required for Specific Interation with Intercellular Adhesion Molecule 1 (ICAM–1)*, (1995) 270:19008–19016.

Huth, J.R., *NMR and Mutagenesis Evidence for an I Domain Allosteric Site That Regulates Lymphocyte Function–associated Antigen 1 Ligand Binding*. Proc. Natl. Acad. Sci, USA (2000) 97:5231–5236.

Kallen, J., et al., *Structural Basis for LFA–1 Inhibition upon Lovastatin Binding to the CD11a I–Domain*, J. Mol. Biol. (1999) 292:1–9.

Kelly, T.A., *Cutting Edge: A Small Molecule Antagonist of LFA–1–Mediated Cell Adhesion*, J. Immunol. (1999) 163:5173–5177.

Kishimoto, T.K., *Integrins, ICAMs and Selectins: Role and Regulation of Adhesion Molecules in Neutrophil Recruitment to Inflammatory Sites*, Adv. Pharmacol. (1994) 25:117–169.

Landis, R.C. *Involvement of The "I" domain of LFA–1 in Selective Binding to Ligands ICAM–I and ICAM–3*, J. Cell Biol. (1994) 126:529–537.

Link, J.T., et al., *Discovery and SAR of Diarylsulfide Cyclopropylamide LFA–1/ICAM–1 Interaction Antagonists*. Bioorg. Med. Chem Lett. (2001) 11:973–976.

Liu, G., *Small Molecule Antagonists of the LFA–1/ICAM–1 Interaction as Potential Therapeutic Agents*, Expert Opin. Ther.Patents (2001) 11(9) 1383–1393.

Liu, G., et al., *Discovery of Novel P–arylthio Cinnamides as Antogonists of Leukocyte Function–associated Antigen–1/intracellular Adhesion Molecule–1 Interaction, 1. Identification of an Additional Binding Pocket Based on an Anilino Diaryl Sulfide Lead*. J. Med. Chem. (2000) 43:4025–4040.

Liu, G., et al., *Novel P–arylthio Cinnamides as Antagonists of Leukocyte Function–associated Antigen–1/intracellular Adhesion Molecule–1 Interaction. 2. Mechanism of Inhibition and Structure–based Improvement of Pharmaceutical Properties*, J. Med. Chem. (2001) 44:1202–1210.

Lu, C., et al., *An Isolated, Surface–expressed I Domain of the Integrin AI$\beta$2 Is Sufficient for Strong Adhesive Function When Locked in the Open Conformation with A Disulfide Bond*. Proc. Natl. Acad. Sci. USA (2001) 98:2387–2392.

Nakano, T., et al., *Adxanthromycins A and B, New Inhibitors of ICAM–1/ILFA–1 Mediated Cell Adhesion Molecule from Streptomyces sp NA–148*, J. Antibos. (Tokyo) (2000) 53:12–18.

Pei, Z., et al., *Discovery of Potent Antagonists of Leukocyte Function–associated Antigen–1/intercellular Adhesion Molecule–1 Interaction. 3. Amide (C–ring) Structure–activity Relationship and Improvement of Overall Properties of Arylthio Cinnamides*. J. Med. Chem. (2001) 44:2913–2920.

Qu, A., et al., *The Role of the Divalent Cation in the Structure of the I Domain from the CD11a/CD18 Integrin*, Structure (1996) 4:931–942.

Sanfilippo, P.J. *Novel Thiazole Based Heterocycles as Inhibitors of LFA–1/ICAM–1 Mediated Cell Adhesion*, J. Med. Chem. (1995) 38:1057–1059.

Springer, T.A., *Adhesion Receptors of the Immune System*, Nature (1990) 346:425–434.

Stanley, P., et al., *The I Domain of Integrin LFA–1 Interacts with ICAM–1 Domain 1 at Residue Glu–34 But Not Gln–73*, J. Biol. Chem. (1998) 273:3358–3362.

Winn, Martin et al., *Discovery of Novel p–Arylthio Cinnamides as Antagolists of Leukocyte Function–Associated Antigen–1/Intercellular Adhesion Molecule–1 Interaction. 4. Structure–Activity Relationship of Substituents on the Benzene Ring of the Cinnamide*, J. Med. Chem. (2001) 44:4393.

Zhu, G., et al., *Diels–Alder Reactions of Hexafluoro–w–butyne with 2–Heterosubstituted Furans: A Facile and General Synthesis of 1,4 Disubstituted 2,3–Di(trifluoromethyl) benzenes*, Organic Letters (2000) vol. 2, No. 21, 3345.

Auodjit, et al., *J Immunol* 161 :2333–2338 (1998).
Bennet, et al., *J Pharmacol Exp Ther* 280 :988–1000 (1997).
Berge, S.M. et al., *J. Pharmaceutical Sciences*, 66 :1 et seq. (1977).
Bicking, et al., *J. Med. Chem.*, 19:534 (1976).
Bloemen, et al., *Am J Respir Crit Care Med* 153:521–529 (1996).
Bowes, et al., *Exp Neurol* 119(2) :215–219 (1993).
Chopp, et al., *Stroke* 25(4): 869–875 (1994).
Clark, et al., *Newurosurg* 75(4) :623–627 (1991).
Cosimi, et al., *J Immunol* 144 :4604–4612 (1990).
DeMeester, et al., *Transplantation* 62(10) :1477–1485 (1996).
Gorczynski, et al., *J Immunol* 152 :2011–2019 (1994).
Gross, et al., *Science* 281 :703–706 (1998).
Gute, et al., *Mol Cell Biochem* 179 :169–187 (1998).
Hallahan, et al., *Proc Natl Acad Sci USA* 94:6432–6437 (1997).
Halloran, et al., *Arthritis Rheum* 39:810–819 (1996).
Harning, et al., *Transplantation* 52:842–845 (1991).
Hartman, et al., *Cardiovasc Res* 30(1) :47–54 (1995).
Hasagawa, et al., *Int Immunol* 6 :831–838 (1994).
He, et al., *Opthalmol vis Sci* 35 :3218–3225 (1994).
Herrold, et al., *Cell Immunol* 157 : 489–500 (1994).
Horgan, et al., *Am J Physiol* 261(5) :H1578–H1584 (1991).
Isobe, et al., *Science* 255 :1125–1127 (1992).
Kakimoto, et al., *Cell Immunol* 142 :326–337 (1992).
Kawasaki, et al., *J Immunol* 150 :1074–1083 (1993).
Knoerzer, et al., *Toxicol Pathol*, 25 :13–19 (1997).
Lawrence, M.B., et al., "Leukocytes' Roll On", *Cell*, 65 :859–873,(1991).
Ley, K., et al., "Lectin–Like Cell", *Blood*, 77:2553–2555 (1991).
March, J., *Advanced Organic Chemistry*, pp. 16–18 (1985).
Mulligan, et al., *J Immunol* 154:1350–1363 (1995).
Nagase, et al., *Am J Respir Crit Care Med* 154:504–510 (1996).
Nakao, et al., *Muslce Nerve* 18 :93–102 (1995).

Oppenheimer–Marks, et al., *J Clin Invest* 101 :1261–1272 (1998).
Panes, et al., *Gastroenterology* 108 :1761–1769 (1995).
Prescott, Ed., *Methods in Cell Biology*, vol. XIV, Acad Press, New York, N.Y., p33 (1976).
Schimmer, et al., *J Immunol* 160 :1466–1477 (1998).
Springer, T.A., "Traffic Signals for", *Cell*, 76:301–314 (1994).
Talento, et al., *Transplantation* 55 :418–422 (1993).
Tamiya, et al., *Immunopharacology* 29(1) :53–63 (1995).
Tanaka, et al., *J Immunol* 151 :5088–5095 (1993).
Von Adrian U., et al., "Two–Step Model", *Proc. Nat'l. Acad. Sci. USA*, 88:7538–7542 (1991).
Wegner, et al., *Lung* 170 :267–279 (1992).
Wegner, et al., *Science* 247 :456–459 (1990).
Zeng, et al., *Transplantation* 58 :681–689 (1994).

* cited by examiner

ARYL PHENYLCYCLOPROPYL SULFIDE DERIVATIVES AND THEIR USE AS CELL ADHESION INHIBITING ANTI-INFLAMMATORY AND IMMUNE SUPPRESSIVE AGENTS

CROSS REFERENCE TO RELATED APPLICATION

This application claims the benefit of provisional U.S. Patent Application Serial No. 60/215,060, filed Jun. 29, 2000.

TECHNICAL FILED

The present invention relates to compounds that are useful for treating inflammatory and immune diseases, to pharmaceutical compositions comprising these compounds, and to methods of inhibiting inflammation or suppressing immune response in a mammal.

BACKGROUND OF THE INVENTION

Inflammation results from a cascade of events that includes vasodilation accompanied by increased vascular permeability and exudation of fluid and plasma proteins. This disruption of vascular integrity precedes or coincides with an infiltration of inflammatory cells. Inflammatory mediators generated at the site of the initial lesion serve to recruit inflammatory cells to the site of injury. These mediators (chemokines such as IL-8, MCP-1, MIP-1, and RANTES, complement fragments and lipid mediators) have chemotactic activity for leukocytes and attract the inflammatory cells to the inflamed lesion. These chemotactic mediators which cause circulating leukocytes to localize at the site of inflammation require the cells to cross the vascular endothelium at a precise location. This leukocyte recruitment is accomplished by a process called cell adhesion.

Cell adhesion occurs through a coordinately regulated series of steps that allow the leukocytes to first adhere to a specific region of the vascular endothelium and then cross the endothelial barrier to migrate to the inflamed tissue (Springer, T. A., 1994, "Traffic Signals for Lymphocyte Recirculation and Leukocyte Emigration: The Multistep Paradigm", Cell, 76: 301–314; Lawrence, M. B., and Springer, T. A., 1991, "Leukocytes' Roll on a Selectin at Physiologic Flow Rates: Distinction from and Prerequisite for Adhesion Through Integrins", Cell, 65: 859–873; von Adrian, U., Chambers, J. D., McEnvoy, L. M., Bargatze, R. F., Arfos, K. E, and Butcher, E. C., 1991, "Two-Step Model of Leukocyte-Endothelial Cell Interactions in Inflammation", Proc. Nat'l. Acad. Sci. USA, 88: 7538–7542; and Ley, K., Gaehtgens, P., Fennie, C., Singer, M. S., Lasky, L. H. and Rosen, S. D., 1991, "Lectin-Like Cell Adhesion Molecule 1 Mediates Rolling in Mesenteric Venules in vivo", Blood, 77: 2553–2555). These steps are mediated by families of adhesion molecules such as integrins, Ig supergene family members, and selectins which are expressed on the surface of the circulating leukocytes and on the vascular endothelial cells. The first step consists of leukocytes rolling along the vascular endothelial cell lining in the region of inflammation. The rolling step is mediated by an interaction between a leukocyte surface oligosaccharide, such as Sialylated Lewis-X antigen (Slex), and a selectin molecule expressed on the surface of the endothelial cell in the region of inflammation. The selectin molecule is not normally expressed on the surface of endothelial cells but rather is induced by the action of inflammatory mediators such as TNF-α and interleukin-1. Rolling decreases the velocity of the circulating leukocyte in the region of inflammation and allows the cells to more firmly adhere to the endothelial cell. The firm adhesion is accomplished by the interaction of integrin molecules that are present on the surface of the rolling leukocytes and their counter-receptors (the Ig superfamily molecules) on the surface of the endothelial cell. The Ig superfamily molecules or CAMs (Cell Adhesion Molecules) are either not expressed or are expressed at low levels on normal vascular endothelial cells. The CAM's, like the selecting, are induced by the action of inflammatory mediators like TNF-alpha and IL-1. The final event in the adhesion process is the extravasation of leukocytes through the endothelial cell barrier and their migration along a chemotactic gradient to the site of inflammation. This transmigration is mediated by the conversion of the leukocyte integrin from a low avidity state to a high avidity state. The adhesion process relies on the induced expression of selectins and CAM's on the surface of vascular endothelial cells to mediate the rolling and firm adhesion of leukocytes to the vascular endothelium.

The interaction of the intercellular adhesion molecule ICAM-1 (cd54) on endothelial cells with the integrin LFA-1 on leukocytes plays an important role in endothelial-leukocyte contact. Leukocytes bearing high-affinity LFA-1 adhere to endothelial cells through interaction with ICAM-1, initiating the process of extravasation from the vasculature into the surrounding tissues. Thus, an agent which blocks the ICAM-1/LFA-1 interaction suppresses these early steps in the inflammatory response. Consistent with this background, ICAM-1 knockout mice have numerous abnormalities in their inflammatory responses.

The present invention discloses compounds which bind to the interaction-domain (I-domain) of LFA-1, thus interrupting endothelial cell-leukocyte adhesion by blocking the interaction of LFA-1 with ICAM-1, ICAM-3, and other adhesion molecules. These compounds are useful for the treatment or prophylaxis of diseases in which leukocyte trafficking plays a role, notably acute and chronic inflammatory diseases, autoimmune diseases, tumor metastasis, allograft rejection, and reperfusion injury.

SUMMARY OF THE INVENTION

The present invention is directed to compounds of the structure

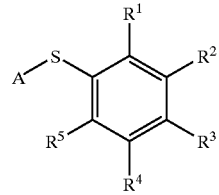

Formula I or pharmaceutically-acceptable salts, optical isomers or prodrugs thereof,
  wherein $R^1$, $R^2$, $R^3$, $R^4$ and $R^5$ are each independently selected from the group consisting of hydrogen, halogen, alkyl, haloalkyl, alkoxy, cyano, nitro, cycloalkyl, carboxaldehyde, "cis-cyclopropanoic acid", "trans-cyclopropanoic acid", "cis-cyclopropanamide", and "trans-cyclopropanamide", wherein
    "cis-cyclopropanoic acid", and "trans-cyclopropanoic acid" are defined as

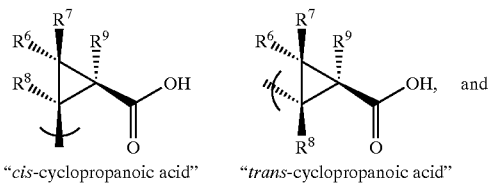

"cis-cyclopropanoic acid"   "trans-cyclopropanoic acid"

"cis-cyclopropanoic acid"   "trans-cyclopropanoic acid", and

"cis-cyclopropanamide", and "Trans-cyclopropanamide" are defined as

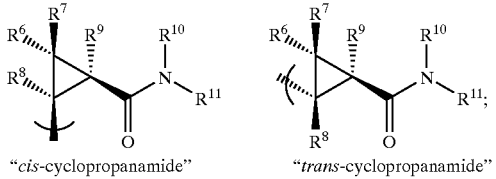

"cis-cyclopropanamide"   "trans-cyclopropanamide"

wherein $R^6$ and $R^7$ are each independently selected from the group consisting of hydrogen, allyl, carboxy, hydroxyalkyl and carboxyalkyl;

$R^8$ and $R^9$ are each independently selected from the group consisting of hydrogen, alkyl, carboxyalkyl, alkylaminocarbonylalkyl and dialkylaminocarbonylalkyl;

and $R^{10}$ and $R^{11}$ are each independently selected from the group consisting of hydrogen, alkyl, cycloalkyl, alkoxycarbonylalkyl, carboxyalkyl, hydroxyalkyl, heterocyclyl, heterocyclylalkyl and heterocyclylamino, or $R^{10}$ and $R^{11}$ are taken together with N to form a three to seven membered unsubstituted heterocyclyl or substituted heterocyclyl ring, substituted with one or more than one substituents $R^{15}$, each substituent $R^{15}$ independently selected from the group consisting of alkyl, alkoxy, alkoxyalkyl, cycloalkyl, aryl, heterocyclyl, heterocyclylcarbonyl, heterocyclylalkylaminocarbonyl, hydroxy, hydroxyalkyl, hydroxyalkoxyalkyl, carboxy, carboxyalkyl, carboxycarbonyl, carboxaldehyde, alkoxycarbonyl, arylalkoxycarbonyl, aminoalkyl, aminoalkanoyl, carboxamido, alkoxycarbonylalkyl, carboxamidoalkyl, cyano, tetrazolyl, alkanoyl, hydroxyalkanoyl, alkanoyloxy, alkanoylamino, alkanoyloxyalkyl, alkanoylaminoalkyl, sulfonate, alkylsulfonyl, alkylsulfonylaminocarbonyl, arylsulfonylaminocarbonyl and heterocyclylsulfonylaminocarbonyl;

and wherein A is an unsubstituted aryl or unsubstituted heterocyclyl group, or a substituted aryl or substituted heterocyclyl group, substituted with one or more than one substituents $R^{12}$, wherein $R^{12}$ is selected from the group consisting of halogen, alkyl, aryl, haloalkyl, hydroxy, alkoxy, alkoxyalkyl, alkoxycarbonyl, alkoxyalkoxy, hydroxyallyl, aminoalkyl, aminocarbonyl, alkyl(alkoxycarbonylalkyl)aminoalkyl, heterocyclyl, heterocyclylalkyl, carboxaldehyde, carboxaldehyde hydrazone, carboxamide, alkoxycarbonylalkyl, carboxy, carboxyalkyl, cycloalkoxy, carboxythioalkoxy, carboxycycloalkoxy, thioalkoxy, carboxyalkylamino, trans-cinnamyl, carboxyalkoxy, hydroxyalkylaminocarbonyl, cyano, amino, heterocyclylalkylamino, and heterocyclylalkylaminocarbonyl;

and wherein $R^1$, $R^2$, $R^3$, $R^4$, $R^5$, $R^6$, $R^7$, $R^8$, $R^9$, $R^{10}$, $R^{11}$, $R^{12}$ and $R^{15}$ are substituted or substituted with at least one electron donating or electron withdrawing group, subject to the proviso that one or more tan one of $R^1$ or $R^3$ is selected from the group consisting of "cis-cyclopropanoic acid", "trans-cyclopropanoic acid", "cis-cyclopropanamide", and "trans-cyclopropanamide" as defined above.

Presently preferred compounds of Formula I have $R^3$ as "cis-cyclopropanamide" or "trans-cyclopropanamide"; $R^4$ and $R^5$ each independently as hydrogen or alkyl; and $R^1$ and $R^2$ each independently as hydrogen, halogen, haloalkyl or nitro.

The present invention is also directed to compounds of the structure

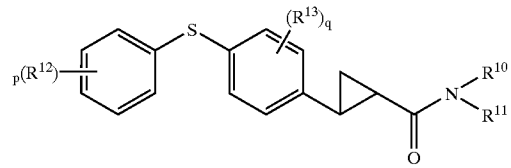

or pharmaceutically-acceptable salts, optical isomers or prodrugs thereof, wherein p is an integer of one to five;

q is an integer of one to four;

$R^{12}$ and $R^{13}$, at each occurrence, are independently selected from the group consisting of hydrogen, halogen, alkyl, haloalkyl, alkoxy, carboxyalkoxy, carboxyalkyl and heterocyclyl;

$R^{10}$ and $R^{11}$ are each independently selected from the group consisting of hydrogen, alkyl, cycloalkyl, alkoxycarbonylalkyl, carboxyalkyl, hydroxyalkyl, heterocyclyl, heterocyclylalkyl and heterocyclylamino, or $R^{10}$ and $R^{12}$ are taken together with N to form a three to seven membered unsubstituted heterocyclyl or substituted heterocyclyl ring, substituted with one or more than one substituents $R^{15}$, each substituent $R^{15}$ independently selected from the group consisting of alkyl, alkoxy, alkoxyalkyl, cycloalkyl, aryl, heterocyclyl, heterocyclylcarbonyl, heterocyclylalkylaminocarbonyl, hydroxy, hydroxyalkyl, hydroxyalkoxyalkyl, carboxy, carboxyalkyl, carboxycarbonyl, carboxaldehyde, alkoxycarbonyl, arylalkoxycarbonyl, aminoalkyl, aminoalkanoyl, carboxamido, alkoxycarbonylalkyl, carboxamidoalkyl, cyano, tetrazolyl, alkanoyl, hydroxyalkanoyl, alkanoyloxy, alkanoylamino, alkanoyloxyalkyl, alkanoylaminoalkyl, sulfonate, alkylsulfonyl, alkylsulfonylaminocarbonyl, arylsulfonylaminocarbonyl and heterocyclylsulfonylaminocarbonyl;

and wherein $R^{10}$, $R^{11}$, $R^{12}$, $R^{13}$ and $R^{15}$ are unsubstituted or substituted with at least one electron donating or electron withdrawing group.

It is preferable, but not required, that when compounds of Formula II have $R^{10}$ and $R^{11}$ taken together with N to form a three to seven membered unsubstituted heterocyclyl or substituted heterocyclyl ring, the ring is piperidine, piperazine, morpholine, pyrrolidine, or azetidine; where p is one; q is one or two; $R^{13}$, at each occurrence is halogen or haloalkyl; and $R^{12}$ is halogen, alkyl, alkoxy, carboxyalkoxy, carboxyalkyl, or heterocyclyl.

Presently preferred, but not required, compounds are of the structure

Formula III

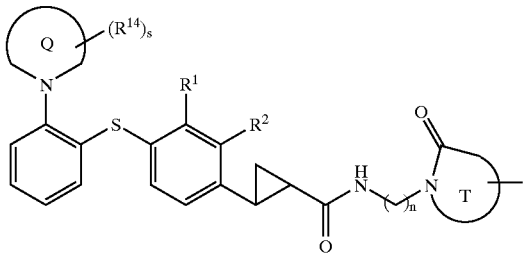

wherein
 the circle Q represents a three to seven membered heterocyclyl ring;
 the circle T represents a five to seven membered heterocyclyl ring;
 r is an integer of one to three;
 s is an integer of one to five;
 n is an integer of one to four;
 $R^1$ and $R^2$, are each independently selected from the group consisting of hydrogen, halogen and haloalkyl;
 $R^{14}$ and $R^{15}$, at each occurrence, are independently selected from the group consisting of hydrogen, halogen, alkyl, alkoxy and carboxy; and
 wherein $R^1$, $R^2$, $R^{14}$ and $R^{15}$ are unsubstituted or substituted with at least one electron donating or electron withdrawing group.

In presently preferred, but not required, compounds of Formula III, circle T is pyrrolidine, n is three; and circle Q is a three to seven membered heterocyclic ring such as piperidine or morpholine.

The compounds represented by structural Formula I, above may be prepared by synthetic processes or by metabolic processes. Processes for the preparation of the compounds of the present invention by metabolic processes include those occurring in the human or animal body (in vivo) or by processes occurring in vitro.

The present invention is also directed to a method of treatment or prophylaxis in which the inhibition of inflammation or suppression of immune response is desired, comprising administering a therapeutic amount of a compound having Formula I; and pharmaceutical compositions containing compounds of Formula I in pharmaceutically acceptable carriers.

DETAILED DESCRIPTION OF THE INVENTION

Definition of Terms

The term "alkanoyl" as used herein refers to an alkyl group attached to the parent molecular group through a carbonyl group.

The term "alkanoylamino" as used herein refers to an alkanoyl group attached to the parent molecular group though an amino group.

The term "alkanoylaminoalkyl" as used herein refers to an alkanoylamino group attached to the parent molecular group through an alkyl group.

The term "alkanoyloxy" as used herein refers to an alkanoyl group attached to the parent molecular group through an oxygen radical.

The term "alkanoyloxyalkyl" as used herein refers to an alkanoyloxy group attached to the parent molecular group through an alkyl group.

The term "alkoxy" as used herein refers to an alkyl group attached to the parent molecular group through an oxygen atom.

The term "alkoxyalkoxy" as used herein refers to an alkoxy group attached to the parent molecular group through an alkoxy group.

The term "alkoxyalkyl" as used herein refers to an alkoxy group attached to the parent molecular group through an alkyl group.

The term "alkoxycarbonyl" as used herein refers to an alkoxy group attached to the parent molecular group through a carbonyl group.

The term "alkoxycarbonylalkyl" as used herein refers to an alkoxycarbonyl group attached to the parent molecular group through an alkyl group.

The term "alkyl" as used herein refers to a saturated straight or branched chain group of 1–10 carbon atoms derived from an alkane by the removal of one hydrogen atom.

The term "alkyl(alkoxycarbonylalkyl)amino" as used herein refers to an amino group substituted with one alkyl group and one alkoxycarbonylalkyl group.

The term "alkyl(alkoxycarbonylalkyl)aminoalkyl" as used herein refers to an alkyl(alkoxycarbonylalkyl)amino group attached to the parent molecular group through an alkyl group.

The term "alkylene" as used herein refers to a divalent group of 1–10 carbon atoms derived from a straight or branched chain alkane by the removal of two hydrogen atoms.

The term "alkylsulfonyl" as used herein refers to an alkyl radical attached to the parent molecular group through an $-SO_2-$ group.

The term "alkylsulfonylaminocarbonyl" as used herein refers to an alkylsulfonyl group attached to the parent molecular group through an aminocarbonyl group.

The term "amino" as used herein refers to a radical of the form $-NR_aR_b$, or to a radical of the form $-NR_a-$, where $R_a$ and $R_b$ are independently selected from hydrogen, alkyl or cycloalkyl.

The term "aminoalkanoyl" as used herein refers to an amino group attached to the parent molecular group through an alkanoyl group.

The term "aminoalkyl" as used herein refers to an amino group attached to the parent molecular group through an alkyl group.

The term "aminocarbonyl" as used herein refers to an amino group attached to the parent molecular group through a carbonyl group.

The term "aryl" as used herein refers to a mono- or bicyclic carbocyclic ring system having one or two aromatic rings. The aryl group can also be fused to a cyclohexane, cyclohexene, cyclopentane or cyclopentene ring. The aryl groups of this invention can be optionally substituted with alkyl, halogen, hydroxy, or alkoxy substituents.

The term "arylalkoxy" as used herein refers to an aryl group attached to the parent molecular group through an alkoxy group.

The term "arylalkoxycarbonyl" as used herein refers to an arylalkoxy group attached to the parent molecular group through a carbonyl group.

The term "arylsulfonyl" as used herein refers to an aryl radical attached to the parent molecular group through an —SO$_2$— group.

The term "arylsulfonylaminocarbonyl" as used herein refers to an arylsulfonyl group attached to the parent molecular group through an aminocarbonyl group.

The term "carboxaldehyde" as used herein refers to the radical —CHO.

The term "carboxaldehyde hydrazone" as used herein refers to the radical —CH=N—NR$_c$R$_d$, where R$_c$ and R$_d$ are independently selected from hydrogen, alkyl or cycloalkyl.

The terms "carboxamide" or "carboxamido" as used herein refer to an amino group attached to the parent molecular group through a carbonyl group.

The term "carboxamidoalkyl" as used herein refers to a carboxamido group attached to the parent molecular group through an alkyl group.

The term "carboxy" as used herein refers to the radical —COOH.

The term "carboxyalkyl" as used herein refers to a carboxy group attached to the parent molecular group through an alkyl group.

The term "carboxyalkylamino" as used herein refers to a carboxyalkyl group attached to the parent molecular group through an amino group.

The term "carboxyalkoxy" as used herein refers to a carboxy group attached to the parent molecular group through an alkoxy group.

The term "carboxycarbonyl" as used herein refers to a carboxy group attached to the parent molecular group through a carbonyl group.

The term "carboxycycloalkoxy" as used herein refers to a carboxy group attached to the parent molecular group through a cycloalkoxy group.

The term "carboxythioalkoxy" as used herein refers to a carboxy group attached to the parent molecular group through a thioalkoxy group.

The term "cyano" as used herein refers to the radical —CN.

The term "cycloalkyl" as used herein refers to a monovalent saturated cyclic or bicyclic hydrocarbon group of 3–12 carbons derived from a cycloalkane by the removal of a single hydrogen atom. Cycloalkyl groups may be optionally substituted with alkyl, alkoxy, halo, or hydroxy substituents.

The term "cycloalkoxy" as used herein refers to a monovalent saturated cyclic or bicyclic hydrocarbon group of 3–12 atoms derived from a cycloalkane by the removal of a single hydrogen atom, linked to the parent molecular group through an oxygen atom. Cycloalkoxy groups may be optionally substituted with alkyl, alkoxy, halo or hydroxy substituents.

The terms "halo" or "halogen" as used herein refers to F, Cl, Br, or I.

The term "haloalkyl" as used herein refers to an alkyl group substituted with one or more halogen atoms.

The terms "heterocycle" or "heterocyclyl" represent a 4-, 5-, 6- or 7-membered ring containing one, two or three heteroatoms independently selected from the group consisting of nitrogen, oxygen and sulfur. The 4- and 5-membered rings have zero to two double bonds and the 6- and 7-membered rings have zero to three double bonds. The term "heterocycle" or "heterocyclic" as used herein additionally refers to bicyclic, tricyclic and tetracyclic groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring. Heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydroquinolyl, tetrazolyl, thiadiazolyl, thiazolidinyl, thiazolyl, thienyl, thiomorpholinyl, triazolyl, and the like.

Heterocyclics also include bridged bicyclic groups where a monocyclic heterocyclic group is bridged by an alkylene group such as

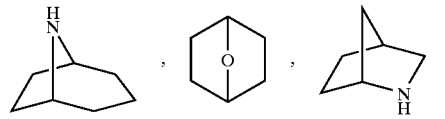

and the like.

Heterocyclics also include compounds of the formula

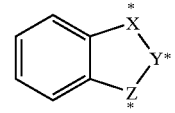

where X* and Z* are independently selected from —CH$_2$—, —CH$_2$NH—, —CH$_2$O—, —NH— and —O—, with the proviso that at least one of X* and Z* is not —CH$_2$13, and Y* is selected from —C(O)13 and —(C(R")2)$_v$—, where R" is hydrogen or alkyl of one to four carbons, and v is 1–3. These heterocycles include 1,3-benzodioxolyl, 1,4-benzodioxanyl, 1,3-benzimidazol-2-one and the like. The heterocycle groups of this invention can be optionally substituted with alkyl, halogen, carboxy, hydroxy or alkoxy substituents.

The term "heterocyclylalkyl" as used herein refers to a heterocyclic group attached to the parent molecular group through an alkyl group.

The term "heterocyclylalkylamino" as used herein refers to a heterocyclylalkyl group attached to the parent molecular group through an amino group.

The term "heterocyclylalkylaminocarbonyl" as used herein refers to a heterocyclylalkylamino group attached to the parent molecular group through a carbonyl group.

The term "heterocyclylamino" as used herein refers to a heterocyclyl group attached to the parent molecular group through an amino group.

The term "heterocyclylcarbonyl" as used herein refers to a heterocyclyl group attached to the parent molecular group through a carbonyl group.

The term "heterocyclylsulfonyl" as used herein refers to a heterocyclyl radical attached to the parent molecular group through an —SO$_2$— group.

The term "heterocyclylsulfonylaminocarbonyl" as used herein refers to a heterocyclylsulfonyl group attached to the parent molecular group through an aminocarbonyl group.

The term "hydroxyalkanoyl" as used herein refers to a hydroxy radical attached to the parent molecular group through an alkanoyl group.

The term "hydroxyalkoxy" as used herein refers to a hydroxy radical attached to the parent molecular group through an alkoxy group.

The term "hydroxyalkoxyalkyl" as used herein refers to a hydroxyalkoxy group attached to the parent molecular group through an alkyl group.

The term "hydroxyalkyl" as used herein refers to a hydroxy radical attached to the parent molecular group through an alkyl group.

The term "hydroxyalkylaminocarbonyl" as used herein refers to a hydroxyalkyl group attached to the parent molecular group through an aminocarbonyl group.

The term "perfluoroalkyl" as used herein refers to an alkyl group in which all of the hydrogen atoms have been replaced by fluoride atoms.

The term "phenyl" as used herein refers to a monocyclic carbocyclic ring system having one aromatic ring. The phenyl group can also be fused to a cyclohexane or cyclopentane ring. The phenyl groups of this invention can be optionally substituted with alkyl, halogen, hydroxy or alkoxy substituents.

The term "pharmaceutically-acceptable prodrugs" as used herein represents those prodrugs of the compounds of the present invention which are, within the scope of sound medical judgment, suitable for use in contact with the tissues of humans and lower animals with undue toxicity, irritation, allergic response. and the like, commensurate with a reasonable benefit/risk ratio, and effective for their intended use, as well as the zwitterionic forms, where possible, of the compounds of the invention.

The term "prodrug," as used herein, represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. The term "sulfonate" as used herein refers to the radical —$SO_3H$.

The term "tetrazole" or "tetrazolyl" as used herein refers to the heterocyclic radical —$CN_4H$.

The term "thioalkoxy" as used herein refers to an alkyl group attached to the parent molecular group through a sulfur atom.

The term "trans-cinnamyl" as used herein refers to an acrylamido group (aminocarbonylethenyl) attached to the parent molecular group through C-3 of the acrylamido group, such that the aminocarbonyl and the parent molecular group exist in a trans relationship about the ethenyl group.

The term "lower" refers to a $C_1$–$C_6$ unit for a particular functionality. For example, "lower alkyl" means $C_1$–$C_6$ alkyl.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogen, trifluoromethoxy, trifluoromethyl, aralkyl, alkenyl, alkynyl, aryl, carboxyalkoxy, carboxyalkyl, cycloalkyl, cycloalkylalkyl, heterocyclyl, alkylheterocyclyl, heterocyclylalkyl, oxo, arylsulfonaminocarbonyl or any of the substituents of the preceding paragraphs or any of those substituents either attached directly or by suitable linkers. The linkers are typically short chains of 1–3 atoms containing any combination of —C—, —C(O)—, —NH—, —S—, —S(O)—, —O—, —C(O)O— or —S(O)—. Rings may be substituted multiple times.

The terms "electron-withdrawing" or "electron-donating" refer to the ability of a substituent to withdraw or donate electrons relative to that of hydrogen if hydrogen occupied the same position in the molecule. These terms are well-understood by one skilled in the art and are discussed in *Advanced Organic Chemistry* by J. March, 1985, pp. 16–18, incorporated herein by reference.

Electron withdrawing groups include halo, nitro, carboxyl, lower alkenyl, lower alkynyl, carboxaldehyde, carboxyamido, aryl, quaternary ammonium and trifluoromethyl among others. Electron donating groups include such groups as hydroxy, lower alkyl, amino, lower alkylamino, di(lower alkyl)amino, aryloxy, mercapto, lower alkylthio, lower alkylmercapto and disulfide among others. One skilled in the art will appreciate that the aforesaid substituents may have electron donating or electron withdrawing properties under different chemical conditions. Moreover, the present invention contemplates any combination of substituents selected from the above-identified groups.

The most preferred electron donating or electron withdrawing substituents are halo, nitro, alkanoyl, carboxaldehyde, arylalkanoyl, aryloxy, carboxyl, carboxamide, cyano, sulfonyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkylamino), amine lower mercapto, mercaptoalkyl, alkylthio and alkyldithio.

As used herein, the term "composition" is intended to encompass a product comprising the specified ingredients in the specified amounts, as well as any product which results, directly or indirectly, from a combination of the specified ingredients in the specified amounts.

Compounds of the present invention can exist as stereoisomers wherein asymmetric or chiral centers are present. These compounds are designated by the symbols "R" or "S," depending on the configuration of substituents around the chiral carbon atom. The present invention contemplates various stereoisomers and mixtures thereof. Stereoisomers include enantiomers and diastereomers, and mixtures of enantiomers or diastereomers are designated (±). Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns.

Geometric isomers can also exist in the compounds of the present invention. The present invention contemplates the various geometric isomers and mixtures thereof resulting from the arrangement of substituents around a carbon-carbon double bond or arrangement of substituents around a carbocyclic ring. Substituents around a carbon-carbon double bond are designated as being in the Z or E configuration wherein the term "Z" represents substituents on the same side of the carbon-carbon double bond and the term "E" represents substituents on opposite sides of the carbon-carbon double bond. The arrangement of substituents around a carbocyclic ring are designated as cis or trans wherein the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated cis/trans.

The compounds of this invention are diaryl sulfides, which are substituted with a cyclopropanoyl or cyclopropanamido moiety. The cyclopropanoyl or cyclopropanamido functionality may be placed either ortho- or para- to the linking sulfur atom, although para-substitution is preferable. Appropriate substitution of both aromatic rings is tolerated, and can be used to modulate a variety of biochemical, physicochemical and pharmacokinetic properties. In particular the amide or carboxyl moiety is readily modified; a variety of secondary and tertiary amides are active, and alternatively a heterocyclic ring may be attached at this position. Modifications of the amide or carboxyl functionality are particularly useful in modulating physicochemical and pharmacokinetic properties.

As is apparent from the foregoing descriptions, the compounds of Formula I are useful in a variety of forms, i.e., with various substitutions as identified. Examples of particularly desirable compounds are quite diverse, and many are mentioned herein. Included are compounds in which $R^1$ is a "cis-cyclopropane" or a "trans-cyclopropane", and $R^3$ is hydrogen; or where $R^3$ is a "cis-cyclopropane" or a "trans-cyclopropane", and $R^1$ is hydrogen, or $R^1$, $R^2$, and $R^4$ are each independently hydrogen or alkyl, and $R^5$ is halogen, haloalkyl or nitro. Further preferred compounds include those as above wherein $R^{10}$ and $R^{11}$ are each independently hydrogen, alkyl, cycloalkyl, alkoxycarbonylaalkyl, hydroxyalkyl, or heterocyclylalkyl, or where $NR^{10}R^{11}$ is heterocyclyl or substituted heterocyclyl, and where A is aryl, substituted aryl, heterocyclyl, or substituted heterocyclyl.

When $R^{10}$ and $R^{11}$ are joined to form a ring, the ring will be heterocyclyl, due to the presence of the nitrogen from which $R^{10}$ and $R^{11}$ are appended. Depending upon which $R^{10}$ and $R^{11}$ substituents are chosen, the ring formed may contain at least one additional heteroatom, such as oxygen, nitrogen or sulfur.

In Formula III, circle Q represents a heterocyclyl, nitrogen containing ring. This ring may contain at least one additional heteroatom, such as oxygen, nitrogen or sulfur; and may be substituted or unsubstituted.

In Formula III, circle T represents a heterocyclyl, amide containing ring. This ring may contain at least one additional heteroatom such as oxygen, nitrogen or sulfur, and may be substituted or unsubstituted.

Compounds of the present invention include, but are not limited to: (±)-(2-bromophenyl)[2-trifluoromethyl-4-(trans-(2-((3-(1-pyrrolidin-2-onyl)-prop-1-ylamino)carbonyl)cycloprop-1-yl)phenyl]sulfide, (±)-(2-isopropylphenyl)[2,3-dichloro-4-(trans-(carboxymethylamino)carbonyl)cycloprop-1-yl)phenyl]sulfide, (±)-(2-isopropylphenyl)[2,3-dichloro-4-(trans-(2-(3-carboxypiperidine))carbonyl)cycloprop-1-yl)phenyl]sulfide, (±)-(2-(2-carboxyethyl)phenyl)[2-trifluoromethyl-4-(trans-(2-((3-(1-pyrrolidin-2-onyl)-prop-1-ylamino)carbonyl)cycloprop-1-yl)phenyl]sulfide, (±)-(2-morpholin-1-ylphenyl)[2-trifluoromethyl-4-(trans-(2-((3-(1-pyrrolidin-2-onyl)-prop-1-ylamino)carbonyl)cycloprop-1-yl)phenyl]sulfide, (±)-(2-morpholin-1-ylphenyl)[2-chloro-4-(trans-(2-((3-(1-pyrrolidin-2-onyl)-prop-1-ylamino)carbonyl)cycloprop-1-yl)phenyl]sulfide, (±)-(2-piperidin-1-ylphenyl)[2-trifluoromethyl-4-(trans-(2-((3-(1-pyrrolidin-2-onyl)-prop-1-ylamino)carbonyl)cycloprop-1-yl)phenyl]sulfide, (±)-(2-pyrrolidin-1-ylphenyl)[2-trifluoromethyl-4-(trans-(2-((3-(1-pyrrolidin-2-onyl)-prop-1-ylamino)carbonyl)cycloprop-1-yl)phenyl]sulfide, (±)-(3-morpholin-1-ylphenyl)[2-trifluoromethyl-4-(trans-(2-((3-(1-pyrrolidin-2-onyl)-prop-1-ylamino)carbonyl)cycloprop-1-yl)phenyl]sulfide, (±)-(2-morpholin-1-ylphenyl)[2,3-dichloro-4-(trans-(2-carboxycycloprop-1-yl)phenyl]sulfide, (±)-(2-morpholin-1-ylphenyl)[2-trifluoromethyl-4-(trans-(2-((3-(1-pyrrolidin-2-onyl)-propyl-N-methylamino)carbonyl)cycloprop-1-yl)phenyl]sulfide, (±)-(2-bromophenyl)[2,3-dichloro-4-(trans-(2-((3-(1-pyrrolidin-2-onyl)-prop-1-ylamino)carbonyl)cycloprop-1-yl)phenyl]sulfide, (±)-(2-bromophenyl)[2,3-dichloro-4-(trans-(2-carboxycycloprop-1-yl)phenyl]sulfide, (±)-(2-isopropylphenyl)[2,3-dichloro-4-(trans-(2-(2-carboxyethylamino)carbonyl)cycloprop-1-yl)phenyl]sulfide, (±)-(2-isopropylphenyl)[2,3-dichloro-4-(trans-(2-(3-carboxypropylamino)carbonyl)cycloprop-1-yl)phenyl]sulfide, (±)-(2-isopropylphenyl)[2,3-dichloro-4-(trans-(2-(4-carboxypiperidin-1-yl)carbonyl)cycloprop-1-yl)phenyl]sulfide, (±)-(2-isopropylphenyl)[2,3-dichloro-4-(trans-(2-(2-carboxypiperidin-1-yl)carbonyl)cycloprop-1-yl)phenyl]sulfide, (±)-(2-isopropylphenyl)[2,3-dichloro-4-(trans-(2-(morpholin-1-yl)carbonyl)cycloprop-1-yl)phenyl]sulfide, (±)-(2-isopropylphenyl)[2,3-dichloro-4-(trans-(2-(4-acetylpiperazin-1-yl)carbonyl)cycloprop-1-yl)phenyl]sulfide, (±)-(2-isopropylphenyl)[2,3-dichloro-4-(trans-(2-((3-(1-pyrrolidin-2-onyl)-prop-1-ylamino)carbonyl)cycloprop-1-yl)phenyl]sulfide, (±)-(2-isopropylphenyl)[2,3-dichloro-4-(trans-(2-(pyrrolidin-1-yl)carbonyl)cycloprop-1-yl)phenyl]sulfide, (±)-(2-isopropylphenyl)[2,3-dichloro-4-(trans-2-(cyclobutylaminocarbonyl)cycloprop-1-yl)phenyl]sulfide, (±)-(2-isopropylphenyl)[2,3-dichloro-4-(trans-(2-(azetidin-1-yl)carbonyl)cycloprop-1-yl)phenyl]sulfide, (±)-(2-isopropylphenyl)[2,3-dichloro-4-(trans-(2-(2-morpholin-1-ylethyl)carbonyl)cycloprop-1-yl)phenyl]sulfide, (2-(3-carboxypiperidin-1-yl)phenyl)[2-trifluoromethyl-4-(trans-(2-((3-(1-pyrrolidin-2-onyl)-prop-1-ylamino)carbonyl)cycloprop-1-yl)phenyl]sulfide, (2-(morpholin-1-yl)phenyl)[2-trifluoromethyl-4-(trans-(2-((3-(1-pyrrolidin-2-onyl)-prop-1-ylamino)carbonyl)cycloprop-1-yl)phenyl]sulfide, (2-(3-carboxypiperidin-1-yl)phenyl)[2,3-dichloro-4-(trans-(2-((3-(1-pyrrolidin-2-onyl)-prop-1-ylamino)carbonyl)cycloprop-1-yl)phenyl]sulfide, (2-methoxyphenyl)[2,3-dichloro-4-(trans-2-(carboxymethylamino)carbonyl)cycloprop-1-yl)phenyl]sulfide, (2-methoxyphenyl)[2,3-dichloro-4-(trans-2-(2-carboxyethylamino)carbonyl)cycloprop-1-yl)phenyl]sulfide, (2-methoxyphenyl)[2,3-dichloro-4-(trans-2-(3-carboxypropylamino)carbonyl)cycloprop-1-yl)phenyl]sulfide, (2-methoxyphenyl)[2,3-dichloro-4-(trans-2-(4-carboxypiperidin-1-yl)carbonyl)cycloprop-1-yl)phenyl]sulfide, (2-methoxyphenyl)[2,3-dichloro-4-(trans-2-(3-carboxypiperidin-1-yl)carbonyl)cycloprop-1-yl)phenyl]sulfide, (2-methoxyphenyl)[2,3-dichloro-4-(trans-2-(2-carboxypiperidin-1-yl)carbonyl)cycloprop-1-yl)sulfide (2-methoxyphenyl)[2,3-dichloro-4-(trans-2-(2-carboxyethylamino)carbonyl)cycloprop-1-yl)phenyl]sulfide, (2-methoxyphenyl)[2,3-dichloro-4-(trans-2-(3-carboxypropylamino)carbonyl)cycloprop-1-yl)phenyl]sulfide, (2-methoxyphenyl)[2,3-dichloro-4-(trans-2-(4-carboxypiperidin-1-yl)carbonyl)cycloprop-1-yl)phenyl]sulfide, (2-methoxyphenyl)[2,3-dichloro-4-(trans-2-(3-carboxypiperidin-1-yl)carbonyl)

cycloprop-1-yl)phenyl]sulfide, (2-methoxyphenyl)[2,3-dichloro-4-(trans-2-(2-carboxypiperidin-1-yl)carbonyl) cycloprop-1-yl)phenyl]sulfide and (2-methoxyphenyl)[2,3-dichloro-4-(trans-(2-((3-(1-pyrrolidin-2-onyl)-prop-1-ylamino)carbonyl)cycloprop-1-yl)phenyl]sulfide.

Abbreviations

Abbreviations which have been used in the schemes and the examples which follow are: DCM for methylene dichloride; EWG for electron withdrawing group; NMP for N-methylpyrrolidinone; sat. for saturated; THF for tetrahydrofuran; TFA for trifluoroacetic acid; ; BINAP for 2,2'-bis(diphenylphosphino)-1,1'-binaphthyl; DMSO for dimethylsulfoxide; DMF for dimethylformamide; TLC for thin layer chromatography; HPLC for high pressure liquid chromatography; APCI for atmospheric pressure chemical ionization; ESI for electrospray ionization; DCI for direct chemical ionization; LFA for lymphocyte function-associated antigen; and ICAM for intercellular adhesion molecule.

Pharmaceutical Compositions and Methods of Treatment

The present invention also provides pharmaceutical compositions which comprise compounds of the present invention formulated together with one or more pharmaceutically-acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically-acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically-acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (I) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically-acceptable emulsions, solutions, suspensions, syrups and elixirs. In addition to the active compounds, the liquid dosage forms may contain inert diluents commonly used in the art such as, for example, water or other solvents. solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

The compounds of the present invention may be used in the form of pharmaceutically-acceptable salts derived from inorganic or organic acids. By "pharmaceutically-acceptable salt" is meant those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically-acceptable salts are well-known in the art. For example, S. M. Berge, et al. Describe pharmaceutically-acceptable salts in detail in J. Pharmaceutical Sciences, 1977, 66:1 et seq. The salts may be prepared in situ during the final isolation and purification of the compounds of the invention or separately by reacting a free base function with a suitable acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically-acceptable basic addition salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically-acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 0.1 to about 50 mg, more preferably of about 5 to about 20 mg of active compound per kilogram of body weight per day are administered orally or intravenously to a mammalian patient. If desired, the effective daily dose may be divided into multiple doses for purposes of administration, e.g. two to four separate doses per day.

Preparation of Compounds of this Invention

The compounds and processes of the present invention may be better understood in connection with the following synthetic schemes which illustrate the methods by which the compounds of the invention can be prepared.

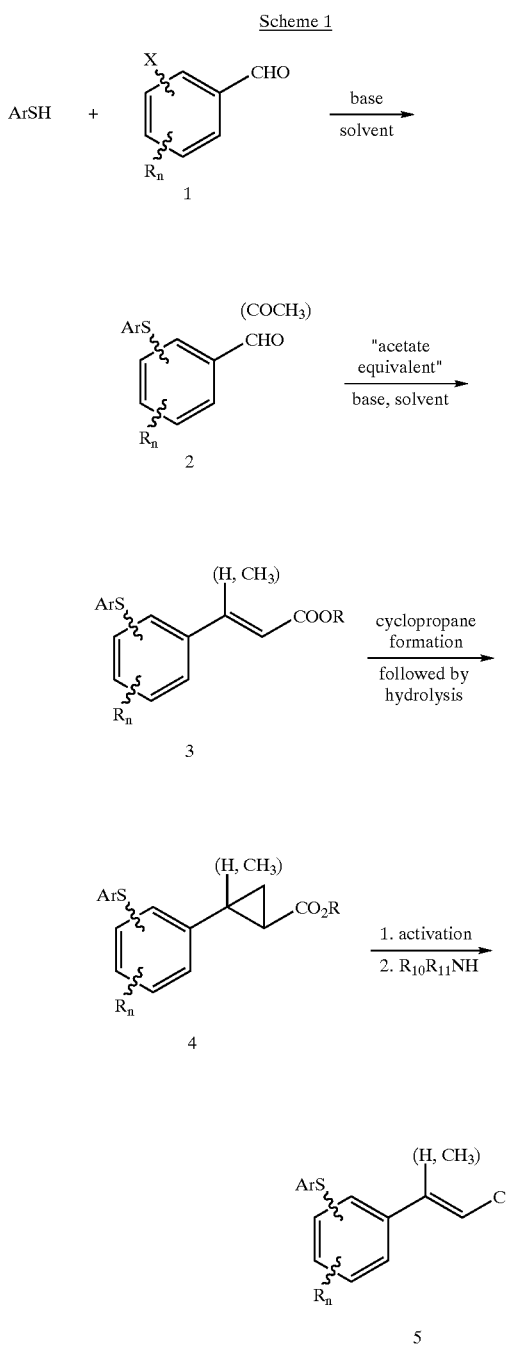

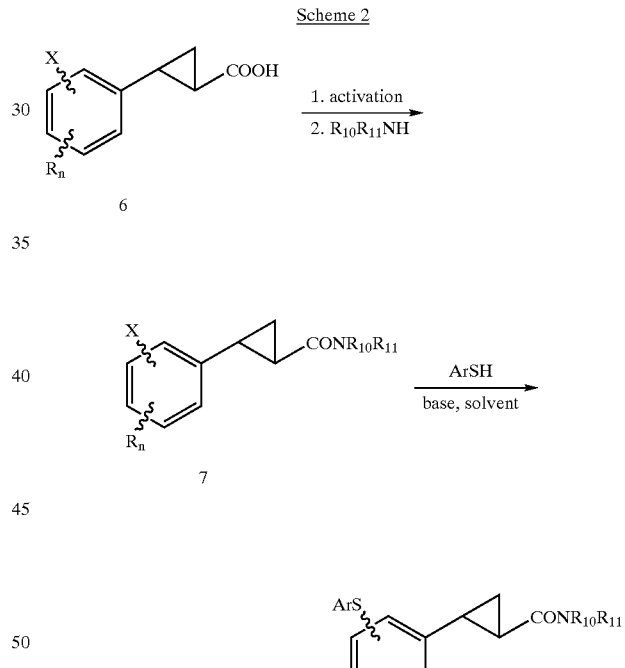

Scheme 1 describes the synthesis of a typical cyclopropane-substituted diaryl sulfide 5 through an aldehyde intermediate 2. Aldehyde 2 is prepared by reaction of a thiophenol (for example 2,4-dichlorothiophenol, 2-bromothiophenol, or the like) with halo-substituted benzaldehyde derivative 1 (e.g. 2-chlorobenzaldehyde, 3-chloro,4-fluorobenzaldehyde, or the like) in the presence of base (e.g. sodium carbonate, triethylamine, or the like) and a polar solvent (e.g. dimethylformamide, dimethylsulfoxide, or the like). The aldehyde group is homologated to the corresponding cinnamic ester 3, using an acetate equivalent (for example, malonic acid, triethoxyphosphonoacetate, or the like) in the presence of an appropriate base and solvent. The cyclopropane acid 4 is prepared by treatment with trimethylsulfoxonium iodide in the presence of base (for example, NaH) followed by hydrolysis of the intermediate ester (for example using sodium hydroxide in alcohol). The acid group is activated (for example using thionyl chloride, or dicyclohexylcarbodiimide and N-hydroxysuccinimide, or the like) and reacted with a primary or secondary amine (for example, 6-aminohexanol, pyrrolidone-3-propylamine, or the like) to provide the desired analog 5. In one variant, a haloacetophenone can replace benzaldehyde 2; the resultant cyclopropanes 5 are substituted with a methyl group.

Alternatively, the order of these coupling steps may be reversed (Scheme 2). A substituted halocyclopropane acid 6 (e.g. 3-chloro-2-nitrocyclopropane acid or the like) may be coupled with a primary or secondary amine (e.g. N-acetylpiperazine or the like) as described above to give the corresponding amide 7. The halo-group can then be displaced with a substituted thiophenol in the presence of base to provide the product 8.

Scheme 3

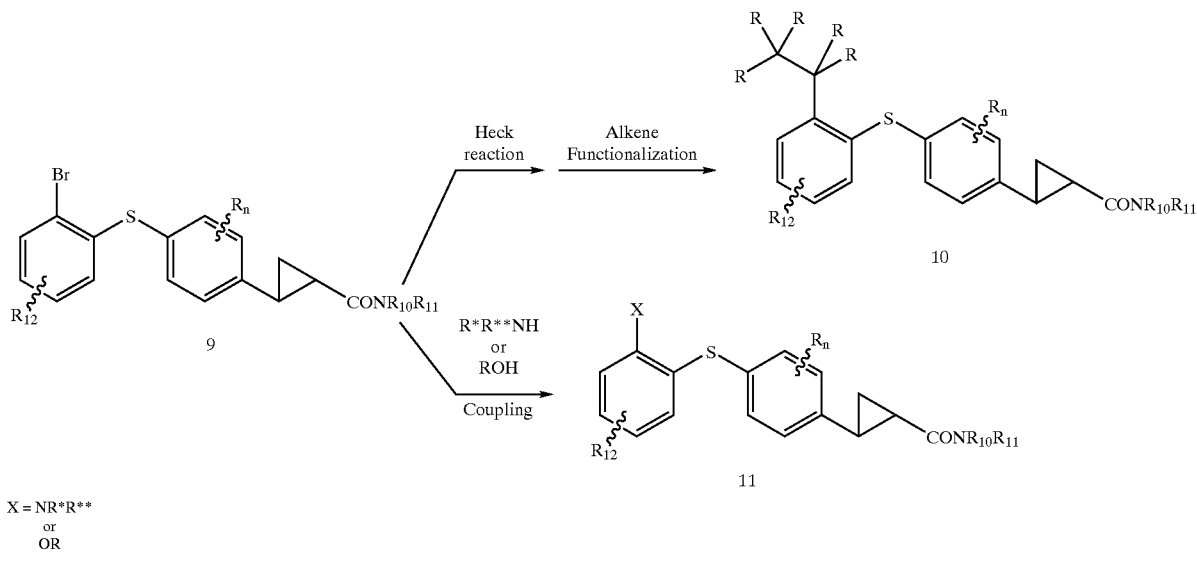

X = NR*R**
or
OR

A number of the compounds described herein may be prepared from intermediate halides or triflates like 9 (Scheme 3) Heck reaction (for example, using palladium acetate and tri-o-tolylphosphine) with alkenes (like methyl acrylate) followed by olefin functionalization (e.g. hydrogenation utilizing palladium on carbon) provides analogs with structures related to 10. Alternatively the halides or triflates may be coupled with amines (primary and secondary) and alcohols under transition metal catalysis (for example tris(dibenzylideneacetone)dipalladium(0) and (±)-2,2' bis(diphenylphosphino)-1,1'-binapthyl) to provide analogs with structures related to 11.

Scheme 4

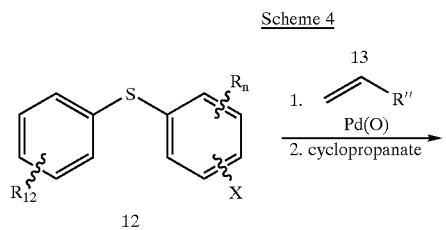

-continued

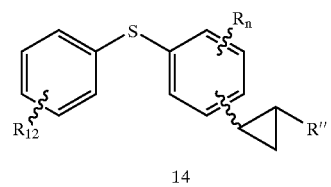

Cyclopropanes like 14 may be prepared from halo(or triflo)-substituted derivatives 12 by palladium-mediated coupling [e.g. using tetrakis(triphenylphosphine) palladium (0), Pd$_2$(dba)$_3$, or the like] with alkene derivatives 13 (Scheme 4). Cyclopropanation (e.g. ethyl diazoacetate and rhodium catalyst) then yields cyclopropanes 14. Direct coupling with cyclopropane derivatives also yields diarylsulfide cyclopropanes 14.

Scheme 5

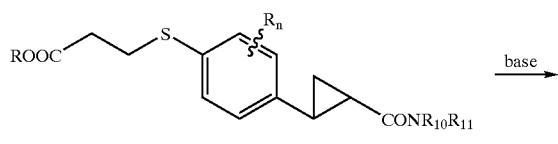

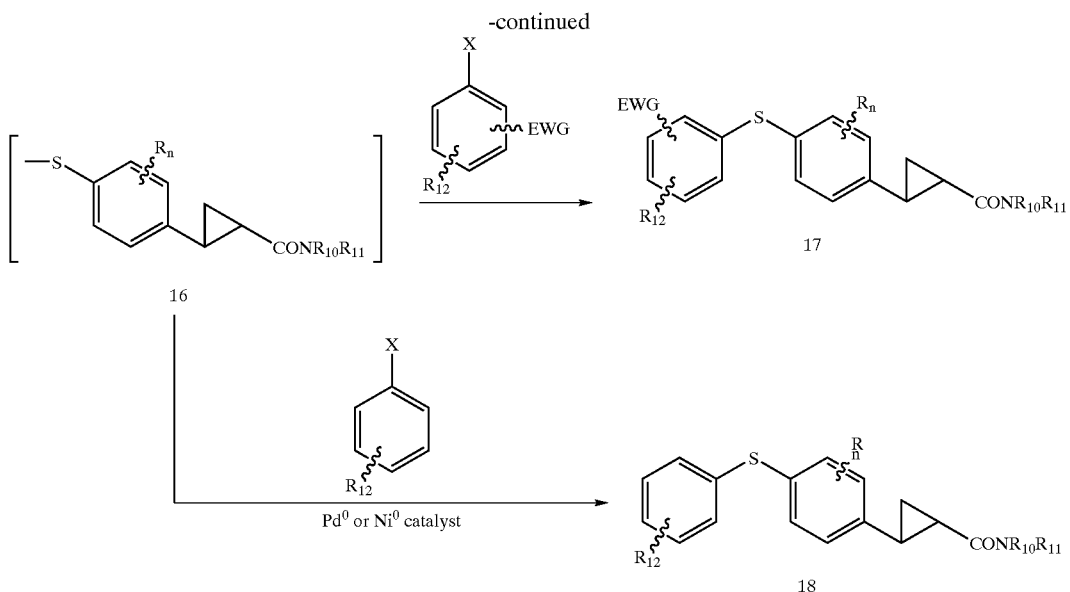

It is also possible to assemble cyclopropane-substituted diaryl sulfides in a "reverse" sense (Scheme 5). Thus, for example, compound 15, prepared as described in Scheme 1, may be deprotected by treatment with base (e.g. potassium t-butoxide or the like) to provide thiolate anion 16, which may be reacted with an activated haloarene (e.g. 2,3-dichlorobenzaldehyde, 3-chloro, 4-fluorobenzaldehyde or the like) to provide the corresponding product 17. Alternatively, this same thiolate anion may be coupled with unactivated aryl halides (e.g. aryl bromide or aryl iodides) using a metal-catalyzed Ullman coupling procedure (for example, using a palladium or nickel catalyst) to give product 18.

The compounds and processes of the present invention will be better understood in connection with the following examples which are intended as an illustration of and not a limitation upon the scope of the invention.

In the Examples, a mixture of isomers is referred to as a compound number, such as compound 1, and the individual isomers are given an A designation (indicating the first isomer, i.e. 1A) or a B designation (indicating the second isomer, i.e. 1B).

EXAMPLE 1

(±)-(2-Bromophenyl)[2-trifluoromethyl-4-(trans-(2-((3-(1-pyrrolidin-2-onyl)-prop-1-ylamino)carbonyl)cycloprop-1-yl)phenyl]sulfide, 19, was synthesized according to the following procedure.

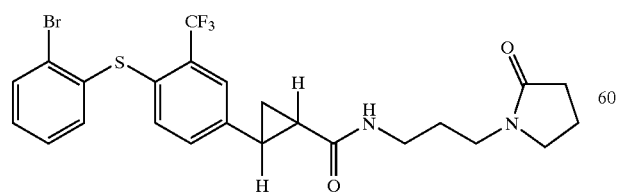

1A. First, 4-[(2-Bromophenyl)thio]-3-trifluoromethyl-benzaldehyde, 20, was synthesized as follows.

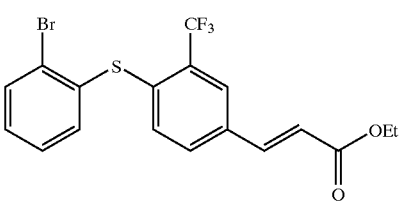

To a stirred solution of potassium carbonate (4.50 g, 32.5 mmol) in 100 mL of anhydrous NMP was added 2-bromothiophenol (3.9 mL, 32.5 mmol), followed by 4-fluoro-3-trifluoromethylbenzaldehyde (5.0 g, 26 mmol). The mixture was heated under nitrogen atmosphere at 85° C. for 12 hours. The reaction mixture was cooled to room temperature and partitioned between ether and water. The aqueous layer was extracted with ether and the combined organic layers washed with water (2×) and brine, dried over sodium sulfate, and condensed in vacuo. The crude product was purified by flash chromatography on silica gel, eluting with 4:1 hexane:ethyl acetate, to give 8.70 g (24.1 mmol, 93%) of the title compound 20 as a yellow oil.

1B. Next, (2-Bromophenyl)[2-trifluoromethyl-4-(E-(ethoxycarbonyl)ethenyl)phenyl]sulfide, 21, was synthesized as follows.

NaH (1.80 g, 45 mmoles, 60% dispersion) was added to a solution of (ethoxycarbonylmethyl)triphenylphosphonium chloride (21.65 g, 45.0 mmoles) in THF (112 mL). After one hour, a solution of the compound 20 (8.70 g, 24.9 mmol) in THF (60 mL) was added dropwise. After one hour the reaction was quenched with sat. NH₄Cl (50 mL) and was concentrated in vacuo. The crude products were dissolved in Et$_2$O, washed with H$_2$O and brine, dried over Na$_2$SO$_4$, filtered, and concentrated in vacuo. Purification by flash chromatography on silica gel eluting with 6.5:1 hexane:ethyl acetate yielded 9.09 g (21.1 mmol, 85%) of the title compound 21 as a yellow oil.

1C. Then (±)-(2-Bromophenyl)[2-trifluoromethyl-4-trans-(2-carboxycycloprop-1-yl)phenyl]sulfide, 22, was synthesized as follows.

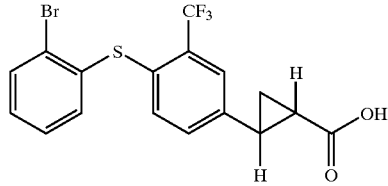

22

NaH (0.7382 g, 18.5 mmoles, 60% dispersion) was added to a solution of trimethylsulfoxonium iodide in DMSO (74 mL). After one hour, a solution of the compound 21 (7.58 g, 17.6 mmol) in DMSO (17.6 mL) was added dropwise. The reaction turned red and was stirred for 12 hours. The crude products were diluted with Et$_2$O and then rinsed with sat. NH$_4$Cl, H$_2$O, and brine. The organic layer was then dried over Na$_2$SO$_4$, filtered, and concentrated in vacuo. Purification by flash chromatography on silica gel using 10:1→4:1 hexane:ethyl acetate as eluant provided 5.09 g (11.4 mmoles, 65%) of cyclopropyl ester. A solution of NaOH (10%, 5.0 mL) was added to a solution of cyclopropyl ester (2.5 g, 5.61 mmoles) in EtOH (20 mL) and THF (5 mL). After one hour, the reaction was quenched with sat. NH$_4$Cl and concentrated in vacuo. The reaction mixture was extracted with EtOAc, rinsed with brine, dried over Na$_2$SO$_4$, filtered, and concentrated in vacuo to provide the title compound 22 (2.29 g, 98%) as a white solid.

1D. Finally, (±)-(2-Bromophenyl)[2-trifluoromethyl-4-(trans-(2-((3-(1-pyrrolidin-2-onyl)-prop-1-ylamino)carbonyl)cycloprop-1-yl)phenyl]sulfide, 19, was synthesized as follows.

1-(3-aminopropyl)-2-pyrrolidinone (0.94 mL, 6.7 mmoles) was added to a solution of the compound 22 (2.0 g, 4.79 mmoles), 1-[3-(dimethylamino)propyl]-3-ethyl carbodiimide hydrochloride (1.1485 g, 5.99 mmoles), and 1-hydroxybenzotriazole hydrate (0.9716 g, 7.2 mmoles) in DMF (18 mL). The reaction was stirred at room temperature overnight. The crude products were diluted with EtOAc and rinsed with sat. NH$_4$Cl, H$_2$O (2×), and brine. The organic layer was dried over Na$_2$SO$_4$ and concentrated. Purification by silica gel chromatography using 9:1 CH$_2$Cl$_2$:MeOH as the eluant yielded 2.4596 g (95%) of the title compound 19. $^1$H NMR (300 MHz, CDCl$_3$) δ7.61 (dd, J=7.7, 1.7 Hz, 1H), 7.50 (d, J=1.8 Hz, 1H), 7.29 (d, J=7.7 Hz, 1H), 7.08–7.22 (m, 3H), 6.96 (dd, J=7.5, 1.7 Hz, 1H), 5.70 (br s, 1H), 3.45 (m, 4H), 3.35 (m, 2H), 2.55 (m, 1H), 2.45 (m, 2H), 2.04–2.18 (m, 2H), 1.66–1.83 (m, 4H), 1.25–1.31 (m, 1H); $^{13}$C NMR (75 MHz, CDCl$_3$) δ176.2, 171.2, 141.9, 135.6, 133.2, 131.3, 130.0, 128.0, 125.02, 125.0, 124.9, 124.8, 124.7, 124.1, 47.4, 39.5, 35.7, 30.8, 27.0, 26.3, 24.1, 17.9, 16.2. MS (APCI) (M+H)$^+$ at m/z 543,421. Anal. Calc'd for C$_{24}$H$_{24}$N$_2$O$_2$SBrF$_3$·1.3 H$_2$O: C, 51.03; H, 4.75; N, 4.96. Found. C, 50.95; H, 4.39; N, 4.94.

EXAMPLE 2

(±)-(2-Isopropylphenyl)[2,3-dichloro-4-(trans-(carboxymethylamino)carbonyl)cycloprop-1-yl)phenyl]sulfide, 23, was synthesized in the following manner.

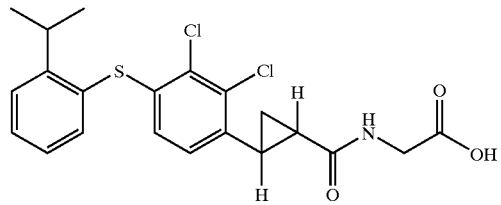

23

2A. First, (2-Isopropylphenyl)[2,3-dichloro-4-formylbenzene]sulfide, 24, was synthesized in the following manner.

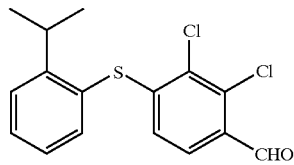

24

Trifluoromethanesulfonic anhydride (5.74 mL, 34.1 mmoles) was added to a suspension of 2,3-dichloro-4-hydroxy-benzaldehyde (synthesized according to the procedure of Bicking et al., *J. Med. Chem.*, 1976, 19, 534, 5.92 g, 31.0 mmoles) in pyridine (31 mL) at 0° C. The reaction was warmed to room temperature and stirred for one hour. The crude products were poured onto ice and extracted with Et$_2$O (2×). The combined organics were washed with 1N HCl (2×) and brine before being dried over Na$_2$SO$_4$. Concentration provided 10 g of the corresponding crude triflate. 2-isopropylbenzenethiol (90% pure, 2.6 mL, 15.5 mmoles) and N,N-diisopropylethylamine (5.4 mL, 31.0 mmoles) were added to a solution of crude triflate (5.0 g, 15.5 mmoles) in CH$_3$CN (15.5 mL). After 20 minutes, the reaction was quenched with sat. NH$_4$Cl. The crude products were extracted with Et$_2$O and washed with sat. Nh$_4$Cl, H$_2$O (2×), and brine. The organic layer was dried with Na$_2$SO$_4$ and concentrated. Flash chromatography on silica gel eluting with 20:1→10:1 hexane:ethyl acetate provided the title compound 24 (3.71 g, 74%).

2B. Then (±)-(2-Isopropylphenyl)[2,3-dichloro-4-trans-(2-carboxycycloprop-1-yl)phenyl]sulfide, 25, was synthesized as follows.

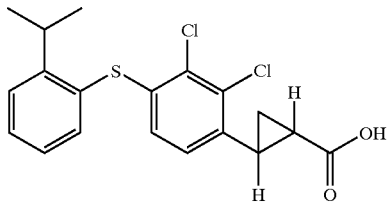

25

25 was prepared from the compound 24 by the procedures described in Example 1, steps B and C. $^1$H-NMR (CDCl$_3$, 300 MHz) δ7.42 (m, 3H), 7.22 (m, 1H), 6.74 (d, J=8.5 Hz, 1H), 6.40 (d, J=8.5, 1H), 3.46 (m, 1H), 2.76 (m, 1H), 1.74 (m, 1H), 1.65 (m, 1H), 1.32 (m, 1H), 1.18 (d, J=6.8 Hz, 6H); $^{13}$C-NMR (CDCl$_3$, 75 MHz) d 179.4, 152.8, 139.4, 136.6, 135.2, 134.9, 130.4, 192.0, 128.0, 127.16, 126.81, 125.22, 124.9, 30.9, 25.7, 23.8, 22.7, 16.1; MS (APCI) (M+HCl)$^{31}$ at m/z 417.

2C. Then (±)-(2-Isopropylphenyl)[2,3-dichloro-4-(trans-(carboxymethylamino)carbonyl)cycloprop-1-yl)phenyl]sulfide, 23, was prepared as follows.

N,N-Diisopropylethylamine (0.11 mL, 0.63 mmoles) was added to a solution of the compound 25 (0.1000 g, 2622 mmoles), 1-[3-(dimethylamino)propyl]-3-ethyl carbodiimide hydrochloride (0.0704 g, 0.367 mmoles), 1-hydroxybenzotriazole hydrate (0.0602 g, 0.4457 mmoles), and glycine methyl ester hydrochloride (0.0658 g, 0.52 mmoles) in DMF (0.66 mL). The reaction was stirred at room temperature overnight. The crude products were diluted with EtOAc and rinsed with sat. $NH_4Cl$, $H_2O$ (2x), and brine. The organic layer was dried over $Na_2SO_4$ and concentrated. The crude products were dissolved in THF (1.0 mL) and EtOH (1.0 mL) and treated with 2N NaOH until ester hydrolysis was complete by TLC. The solution was poured into 2N HCl and extracted with EtOAc (2x). The combined organic layers were rinsed with brine, dried over $Na_2SO_4$, concentrated, and purified by preparative HPLC. Reverse phase preparative HPLC was performed on a YMC Guardpak ODS column using acetonitrile and 0.1% trifluoroacetic acid in water as eluant to give 0.0962 g of the title compound 23 (0.22 mmoles, 84%). $^1$H-NMR (CDCl$_3$, 300 MHz) δ7.42 (m, 3H), 7.22 (m, 1H), 6.74 (d, J=8.5 Hz, 1H), 6.40 (d, J=8.5, 1H), 6.22 (t, J=6.8, 1H), 4.17 (dd, J=5.1, 1.7 Hz, 2H), 3.46 (m, 1H), 2.67 (m, 1H), 1.64 (m, 1H), 1.52 (m, 1H), 1.25 (m, 1H), 1.18 (d, J=6.8 Hz, 6H); MS (APCI) (M)$^+$ at m/z 440, 438; Anal. Calc'd for $C_{21}H_{21}NO_3SCl_2.0.1$ $H_2O.0.15$ TFA; C, 55.95; H, 4.71; N, 3.06. Found: C, 55.94; H, 4.69; N, 3.13.

EXAMPLE 3

(±)-(2-Isopropylphenyl)[2,3-dichloro-4-(trans-(2-(3-carboxypiperidine))carbonyl)cycloprop-1-yl)phenyl]sulfide, 26, was synthesized according to the following procedure.

26

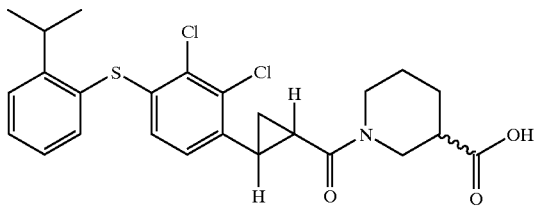

DMF (1 drop) was added to a solution of the compound 25 (0.65 g, 1.7 mmoles) and oxalyl chloride (0.16 mL, 1.87 mmoles) in $CH_2Cl_2$ (4.3 mL). The solution was stirred at room temperature for two hours, concentrated in vacuo, and azeotropically dried with toluene (2x) on a rotary evaporator. The resulting crude acid chloride was dissolved in $CH_2Cl_2$ (5.2 mL). A portion of the solution (0.4 mL) was placed in a separate reaction vessel via syringe and was treated with ethyl nipecotate (0.081 mL, 0.2622 mmoles) and N,N-diiopropylethylamine. After stirring for one hour the reaction was concentrated in vacuo. The crude products were dissolved in THF (1.0 mL) and EtOH (1.0 mL) and treated with 2N NaOH until ester hydrolysis was complete by TLC. The solution was poured into 2N HCl and extracted with EtOAc (2x). The combined organic layers were rinsed with brine, dried over $Na_2SO_4$, concentrated, and purified by preparative HPLC. Preparative HPLC was performed as in Example 2, step C to give 0.0555 g of the title compound 26 (86%) as a white solid. $^1$H-NMR (CDCl$_3$, 300 MHz) δ7.44 (m, 3H), 7.22 (m, 1H), 6.77 (d, J=8.5 Hz, 1H), 6.40 (d, J=8.5, 1H), 4.51 (m, 1H), 4.08 (m, 1H), 3.88 (m, 2H), 3.48 (m, 1H), 3.24 (m, 2H), 2.58 (m, 2H), 2.04–2.22 (m, 3H), 1.64–1.82 (m, 2H). 1.22 (m, 1H), 1.18 (d, J=6.8 Hz, 6H), MS (APCI) (M)$^+$ at m/z 494.492 Anal. Calcd for $C_{25}H_{27}NO_3SCl_2.0.15$ $H_2O.0.15$ TFA: C, 59.32; H, 5.40; N, 2.73. Found: C, 59.32; H, 5.44; N, 2.54.

EXAMPLE 4

(2-Bromophenyl)[2-trifluoromethyl-4-(trans-(2-((3-(1-pyrrolidin-2-onyl)-prop-1-ylamino)carbonyl)cycloprop-1-yl)phenyl]sulfide, Isomer #1, 19A, was synthesized according to the following procedure.

Resolution of the compound 19 using a Chiralpak AD HPLC column eluting with 90:10 hexane:EtOH gave baseline resolution of two enantiomers which were both >98% ee by HPLC. The earlier eluting isomer is denoted isomer #1 (19A) and the later eluting isomer is denoted isomer #2 (19B). $^1$H-NMR (DMSO-d$_6$, 300 MHz) δ8.14 (t, J=5.5 Hz, 1H), 7.71 (dd, J=8.1, 1.5 Hz, 1H), 7.67 (d, J=1.8 Hz, 1H), 7.46 (dd, J=8.5, 1.8 Hz, 1H), 7.35 (d, J=8.1 Hz, 1H), 7.33 (dt, J=7.7, 1.5 Hz, 1H), 7.22 (dt, J=7.7, 1.5 Hz, 1H), 6.85 (dd, J=7.7, 1.5, 1H), 3.28 (m, 4H), 3.17 (t, J=7.2, 2H), 3.05 (m, 2H), 2.41 (m, 1H), 2.20 (t, J=6.6 Hz, 2H), 1.92 (m, 1H), 1.58 (m, 2H), 1.43 (m, 1H), 1.35 (m, 1H), MS (APCI) (M)$^+$ at m/z 543, 541.

EXAMPLE 5

(2-Bromophenyl)[2-trifluoromethyl-4-(trans-(2-((3-(1-pyrrolidin-2-onyl)-prop-1-ylamino)carbonyl)cycloprop-1-yl)phenyl]sulfide, Isomer #2, 19B, was also isolated from the procedure described in Example 4. $^1$H-NMR (DMSO-d$_6$, 300 MHz) δ8.14 (t, J=5.5 Hz, 1H), 7.71 (dd, J=8.1., 1.5 Hz,1 H), 7.67 (d, J=1.8 Hz, 1H), 7.46 (dd, J=8.5, 1.8 Hz, 1H), 7.35 (d, J=8.1 Hz, 1H), 7.33 (dt, J=7.7, 1.5 Hz, 1H), 7.22 (dt, J=7.7, 1.5 Hz, 1H), 6.85 (dd, J=7.7, 1.5, 1H), 3.28 (m, 4H), 3.17 (t, J=7.2, 2H), 3.05 (m, 2H), 2.41 (m, 1H), 2.20 (t, J=6.6 Hz, 2H), 1.92 (m, 1H), 1.58 (m, 2H), 1.43 (m, 1H), 1.35 (m, 1H), MS (APCI) (M)$^+$ at m/z 543, 541; FAB HRMS (M+H)$^+$ calc for $C_{24}H_{25}N_2O_2F_3S_1Br_1$ 543.0752, obs. 543.0762; Anal. Calc'd for $C_{24}H_{24}N_2O_2SF_3Br.1.6$ $H_2O$: C, 50.55; H, 4.81; N, 4.91. Found: C, 50.33; H, 4.28; N, 4.76.

EXAMPLE 6

(±)-(2-(2-carboxyethyl)phenyl)[2-trifluoromethyl-4-(trans-(2-((3-(1-pyrrolidin-2-onyl)-prop-1-ylamino)carbonyl)cycloprop-1-yl)phenyl]sulfide, 27, was synthesized according to the following procedure.

27

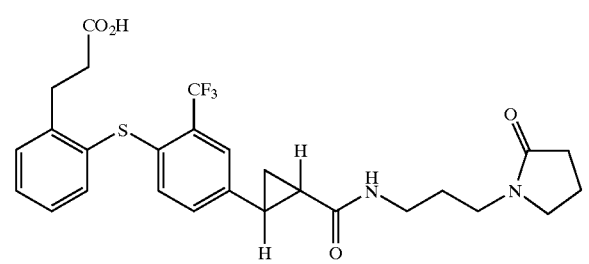

Triethylamine (0.074 mL, 0.53 mmoles) and methyl acrylate (0.048 mL, 0.53 mmoles) were added to a solution of the compound 19 (0.1200 g, 0.2216 mmoles), palladium acetate (0.0025 g, 0.011 mmoles), and tri(o-tolyl)phosphine (0.0202 g, 0.0604 mmoles) in NMP (1.0 mL). The reaction was heated to 85° C. for ten hours. The reaction was diluted with Et₂O and washed with sat. NH₄Cl, H₂O (2×), and brine. The organic layer was dried over Na₂SO₄ and concentrated in vacuo. The crude products were dissolved in THF (1.4 mL) and EtOH (1.4 mL) and were treated with 2N NaOH until ester hydrolysis was complete by TLC. The reaction mixture was then poured into 2N HCl and extracted with EtOAc (2×). The combined organics were dried over Na₂SO₄ and concentrated in vacuo. A solution of the crude products and 10% palladium on carbon (0.0400 g) in EtOAc (1.0 mL) and MeOH (1.0 mL) were stirred vigorously under a hydrogen atmosphere overnight. The reaction was then placed under a nitrogen atmosphere and the crude products filtered through a 1" pad of silica gel with 9:1 CH₂Cl₂:MeOH. Purification by preparative HPLC provided the desired acid 27 (0.0627 g, 53%). ¹H NMR (300 MHz, DMSO-d₆) δ8.12 (br m, 1H), 7.21–7.56 (m, 6H), 6.92 (d, J=8.5 Hz, 1H), 3.18 (m, 2H), 3.04 (m, 2H), 3.30 (m, 2H), 2.90 (t, J=7.7 Hz, 2H), 2.33 (m, 2H), 2.19 (t, J=8.3 Hz, 2H), 1.89 (m, 4H), 1.58 (m, 2H), 1.38 (m, 1H), 1.29 (m, 1H); MS (APCI) (M+H)⁺ at m/z 535.

EXAMPLE 7

(±)-(2-Morpholin-1-ylphenyl)[2-trifluoromethyl-4-(trans-(2-((3-(1-pyrrolidin-2-onyl)-prop-1-ylamino)carbonyl)cycloprop-1-yl)phenyl]sulfide, 28, was synthesized according to the following procedure.

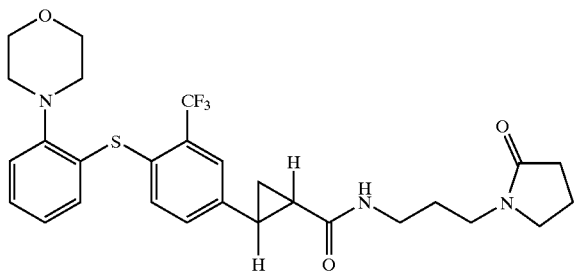

28

Morpholine (0.041 mL, 0.47 mmoles) was added to a solution of the compound 19 (0.2050 g, 0.38 mmoles), tris(dibenzylideneacetone)bispalladium (0.0086 g, 0.0094 mL), (±)-BINAP (0.0176 g, 0.0283 mmoles), and sodium tert-butoxide (0.0509 g, 0.53 mmoles) in toluene (1.5 mL). The reaction was stirred at room temperature for 20 minutes and then at 80° C. for 12 hours. The crude products were filtered through a pad of silica gel with EtOAc followed by 9:1 CH₂C₂:MeOH and purified by preparative HPLC to provide the product 28 (0.740 g, 84%). ¹H NMR (300 MHz, CDCl₃) δ7.45 (d, J=1.8 Hz, 1H), 7.07–7.24 (m, 4H), 6.97 (dt, J=7.5, 1.5 Hz, 1H), 6.84 (dd, J=8.1 1.5 Hz, 1H), 3.78 (t, J=4.6 Hz, 4H), 3.42 (m, 4H), 3.17–3.37 (m, 4H), 3.05 (t, J=4.4 Hz, 4H), 2.53 (m, 1H), 2.47 (m, 2H), 2.09 (m, 2H), 1.72 (m, 3H), 1.25 (m, 1H); MS (APCI) (M+H)⁺ at m/z 548; Anal. Calc'd for C₂₈H₃₂N₃O₃SF₃.2.7 H₂O: C, 56.40; H, 6.32; N, 7.05 Found: C, 56.29; H, 5.24; N, 6.61.

EXAMPLE 8

(±)-(2-Morpholin-1-ylphenyl)[2-chloro-4-(trans-(2-((3-(1-pyrrolidin-2-onyl)-prop-1-ylamino)carbonyl)cycloprop-1-yl)phenyl]sulfide, 29, was synthesized according to the following procedure.

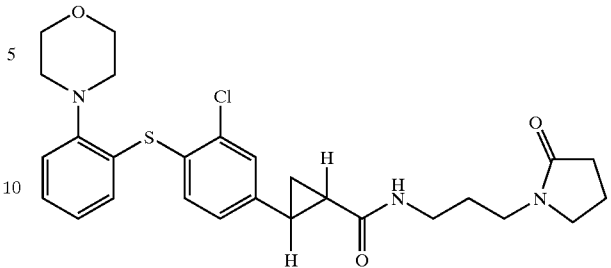

29

The title compound 29 was prepared by the procedure described in Examples 1 and 7, substituting 3,4-dichlorobenzaldehyde for 4-fluoro-3-trifluoromethylbenzaldehyde. ¹H NMR (300 MHz, DMSO-d₆) δ8.14 (t, J=5.5 Hz, 1H), 7.42 (d, J=1.8 Hz, 1H), 7.28 (d, J=8.1 Hz, 1H), 7.12–7.26 (m, 3H), 7.00 (m, 1H), 6.65 (dd, J=7.1, 1.1 Hz, 1H), 3.67 (t, J=4.4 Hz, 4H), 3.30 (m, 2H), 3.17 (t, J=7.2 Hz, 1H), 3.04 (m, 2H), 2.96 (t, J=4.6 Hz, 4H), 2.29 (m, 1H), 2.20 (t, J=8.1 Hz, 2H), 1.92 (m, 3H), 1.58 (m, 2H), 1.48 (m, 1H), 1.39 (m, 1H): MS (APCI) (M+H)⁺ at m/z 514.

EXAMPLE 9

(±)-(2-Piperidin-1-ylphenyl)[2-trifluoromethyl-4-(trans-(2-((3-(1-pyrrolidin-2-onyl)-prop-1-ylamino)carbonyl)cycloprop1-yl)phenyl]sulfide, 30, was synthesized according to the following procedure.

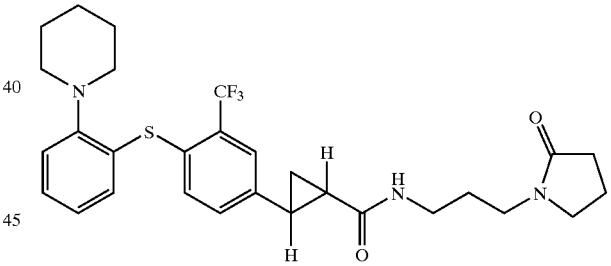

The title compound 30 was prepared by the procedure described in Example 7, substituting piperidine for morpholine. ¹H NMR (300 MHz, DMSO-d₆) δ8.15 (t, J=7.1 Hz, 1H), 7.61 (d, J=1.8 Hz, 1H), 7.41 (dd, J=8.3, 1.7 Hz, 1H), 7.35 (d, J=8.1 Hz, 1H), 7.18 (m, 2H), 6.95 (m, 1H), 6.61 (dd, J=7.7, 1.1 Hz, 1H), 3.31 (m, 2H), 3.17 (t, J=7.2 Hz, 2H), 3.05 (m, 2H), 2.90 (t, J=4.6 Hz, 4H), 2.38 (m, 1H), 2.20 (t, J=7.9 Hz, 2H), 1.92 (m, 3H), 1.59 (m, 6H), 1.50 (m, 2H), 1.42 (m, 1H), 1.32 (m, 1H); MS (APCI) (M+H)⁺ at m/z 546.

EXAMPLE 10

(±)-(2-Pyrrolidin-1-ylphenyl)[2-trifluoromethyl-4-(trans-(2-((3-(1-pyrrolidin-2-onyl)-prop-1-ylamino)carbonyl)cycloprop-1-yl)phenyl]sulfide, 31, was synthesized according to the following procedure.

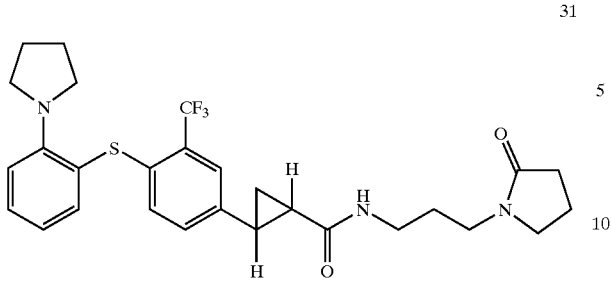

31

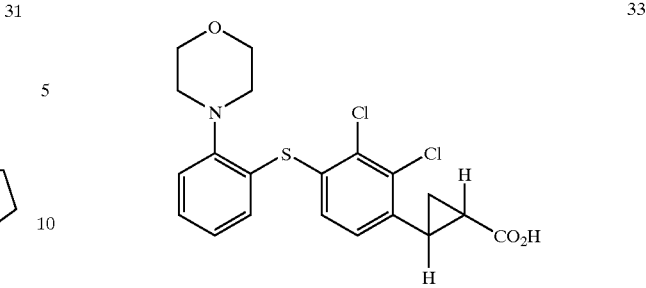

33

The title compound 31 was prepared by the procedure described in Example 7, substituting pyrrolidine for morpholine. $^1$H NMR (300 MHz, DMSO-$d_6$) δ8.07 (m, 1H), 7.47 (d, J=1.7 Hz, 1H), 7.23–7.32 (m, 2H), 7.16 (dd, J=7.5, 1.4 Hz, 1H), 6.97 (d, J=8.1 Hz, 1H), 6.75–6.83 (m, 2H), 3.16 (t, J=4.4 Hz, 4H), 3.30 (m, 2H), 3.17 (t, J=7.2 Hz, 1H), 3.04 (m, 2H), 2.96 (t, J=4.6 Hz, 4H), 2.29 (m, 1H), 2.20 (t, J=7.1 Hz, 2H), 3.03 (m, 2H), 2.28 (m, 1H), 2.19 (t, J=8.0 Hz, 2H), 1.82–1.94 (m, 4H), 1.76–1.80 (m, 4H), 1.55–1.62 (m, 2H), 1.35 (m, 1H), 1.23 (m, 1H); MS (APCI) (M+H)$^+$ at m/z 532.

The title compound 33 was prepared first by the procedure described in Example 2, substituting 2-bromobenzenethiol for 2-isopropylbenzenethiol. The resultant aldehyde was converted to the corresponding cyclopropanecarboxylic acid according to Example 1, steps 1B and 1C. The title compound was then prepared following Example 7. $^1$H NMR (300 MHz, DMSO-$d_6$) δ7.34 (dt, J=7.8, 1.7 Hz, 1H), 7.22 (dd, J=7.8, 1.4 Hz, 1H), 6.97–7.12 (m, 4H), 3.58 (t, J=4.4 Hz, 4H), 2.95 (t, J=4.4 Hz, 4H), 2.58 (m, 1H), 1.74 (m, 1H), 1.45 (t, J=6.3, 2H); MS (APCI) (M)$^+$ at m/z 424.

EXAMPLE 11

(±)-(3-Morpholin-1-ylphenyl)[2-trifluoromethyl-4-(trans-(2-((3-(1-pyrrolidin-2-onyl)-prop-1-ylamino)carbonyl)cycloprop-1-yl)phenyl]sulfide, 32, was synthesized according to the following procedure.

EXAMPLE 13

(±)-(2-Morpholin-1-ylphenyl)[2-trifluoromethyl-2-(trans-(2-((3-(1-pyrrolidin-2-onyl)-propyl-N-methylamino)carbonyl)cycloprop-1-yl)phenyl]sulfide, 34, was synthesized according to the following procedure.

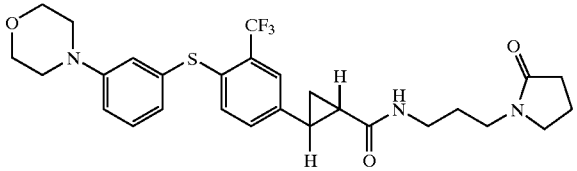

32

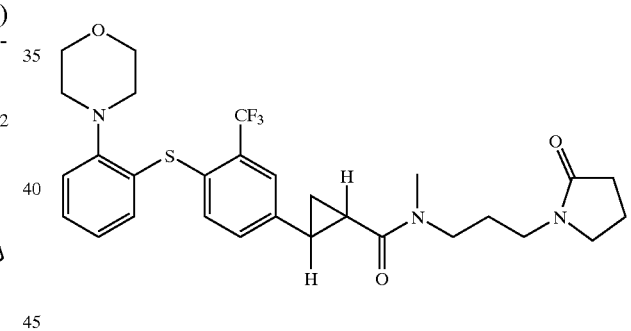

34

The title compound 32 was prepared by the procedures described in Examples 1 and 7 substituting 3-bromobenzenethiol for 2-bromobenzenethiol. $^1$H NMR (300 MHz, DMSO-$d_6$) δ8.09 (t, J=5.6 Hz, 1H), 7.54 (d, J=1.7 Hz, 1H), 7.34 (dd, J=8.3, 1.9 Hz, 1H), 7.24 (m, 1H), 7.19 (d, J=8.5 Hz, 1H), 6.94 (m, 2H), 6.67 (m, 1H), 3.71 (t, J=4.9 Hz, 4H), 3.16 (t, J=7.1 Hz, 2H), 3.30 (m, 2H), 3.10 (t, J=4.9 Hz, 4H), 3.05 (m, 2H), 2.34 (m, 1H), 2.19 (t, J=8.0 Hz, 2H), 1.89 (m, 3H), 1.58 (m, 2H); MS (APCI) (M+H)$^+$ at m/z 548.

Sodium hydride (60% dispersion, 0.0096 g, 0.241 mmoles) was added to a solution of compound 28 (0.1200 g, 0.219 mmoles) in DMF (0.55 mL). After 15 minutes, iodomethane (0.026 mL, 0.42 mmoles) was added. After four hours, the reaction was diluted with Et$_2$O and washed with sat. NH$_4$Cl, H$_2$O (2×), and brine. The organic layer was dried Na$_2$SO$_4$ and concentrated in vacuo. Purification by preparative HPLC provided the title compound 34 (0.0922 g, 75%). $^1$H NMR (300 MHz, DMSO-$d_6$) δ7.45 (d, J=1.5 Hz, 1H), 7.16–7.37 (m, 3H), 7.09 (dd, J=8.1, 1.1 Hz, 1H), 6.98 (dt, J=7.3, 1.3 Hz, 3H), 6.83–6.91 (m, 1H), 3.76 (t, J=4.4 Hz, 4H), 3.32–3.51 (m, 6H), 3.17 (s, 2H), 3.06 (t, J=4.4 Hz, 4H), 3.00 (s, 1H), 2.45–2.59 (m, 3H), 1.99–2.25 (m, 3H), 1.65–1.94 (m, 3H), 1.31–1.38 (m, 1H); MS (APCI) (M+H)$^+$ at m/z 562.

EXAMPLE 12

(±)-(2-Morpholin-1-ylphenyl)[2,3-dichloro-4-(trans-(2-carboxycycloprop-1-yl)phenyl]sulfide, 33, was synthesized according to the following procedure.

EXAMPLE 14

(±)-(2-Bromophenyl)[2,3-dichloro-4-(trans-(2-((3-(1-pyrrolidin-2-onyl)-prop-1-ylamino)carbonyl)cycloprop-1-yl)phenyl]sulfide, 35, was synthesized according to the following procedure.

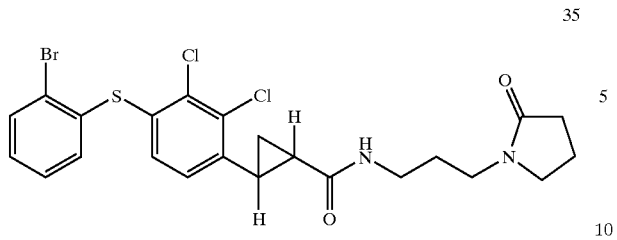

35

The title compound 35 was prepared by the procedure described in Example 2, substituting 2-bromobenzenethiol for 2-isopropylbenzenethiol. The resultant aldehyde was then converted to the title compound by following the procedures of Example 1, steps 1B, 1C, and 1D. $^1$H NMR (300 MHz, CDCl$_3$) δ7.56 (dd, J=8.4, 1.3 Hz, 1H), 7.18 (dt, J=7.2, 1.4 Hz, 1H), 7.08 (m, 2H), 7.03 (br s, 1H), 6.81 (d, J=8.5 Hz, 1H), 6.77 (d, J=8.0 Hz, 1H), 3.21–3.34 (m, 5H), 3.11 (m, 1H), 2.60 (m, 1H), 2.32 (t, J=8.0 Hz, 2H), 1.98 (m, 2H), 1.62 (t, J=5.9 Hz, 2H), 1.52 (m, 2H), 1.12 (m, 1H); $^{13}$C NMR (75 MHz, CDCl$_3$) d 176.0, 171.4, 139.5, 135.2, 134.7, 133.9, 133.6, 133.3, 132.95, 129.2, 129.1, 128.3, 127.3, 125.5, 47.5, 39.6, 35.7, 30.9, 26.5, 25.4, 23.9, 17.9, 14.2; MS (APCI) (M+H)$^+$ at m/z 543; Anal. Calc'd for C$_{23}$H$_{23}$N$_2$O$_2$SCl$_2$Br.0.6 H$_2$O: C, 49.94; H, 4.41; N, 5.06. Found: C, 49.94; H, 4.04; N, 4.85.

EXAMPLE 15

(±)-(2-Bromophenyl)[2,3-dichloro-4-(trans-(2-carboxycycloprop-1-yl)phenyl]sulfide, 36, was synthesized according to the following procedure.

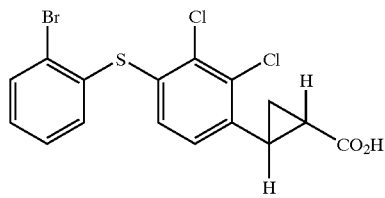

36

The title compound 36 was prepared by the procedure described in Example 2, substituting 2-bromobenzenethiol for 2-isopropylbenzenethiol. The resultant aldehyde was then converted to the title compound by following the procedure of Example 1, steps 1B and 1C. $^1$H NMR (300 MHz, DMSO-d$_6$) δ7.79 (dd, J=8.1, 1.3 Hz, 1H), 7.42 (dt, J=7.6, 1.7 Hz, 1H), 7.34 (dt, J=7.6, 2.1 Hz, 1H), 7.25 (dd, J=7.6, 1.7 Hz, 1H), 7.14 (d, J=8.5 Hz, 1H), 6.94 (d, J=8.1 Hz, 1H), 3.36 (br s, 1H), 2.58 (m, 1H), 1.79 (m, 1H), 1.46 (m, 2H); $^{13}$C NMR (75 MHz, CDCl$_3$) δ173.6, 138.9, 133.8, 133.7, 133.2, 133.1, 133.0, 131.7, 130.2, 129.4, 129.1, 126.3, 125.6, 24.05, 22.94, 15.12 MS (APCI) (M+H)$^-$ at m/z 453; Anal. Calc'd for C$_{16}$H$_{11}$O$_2$BrCl$_2$S.0.05 H$_2$O: C, 45.86; H, 2.67; N, 0.00. Found: C, 45.8; H, 2.49; N, 0.0.

EXAMPLE 16

(±)-(2-Isopropylphenyl)[2,3-dichloro-4-(trans-(2-(2-carboxyethylamino)carbonyl)cycloprop-1-yl)phenyl] sulfide, 37, was synthesized according to the following procedure.

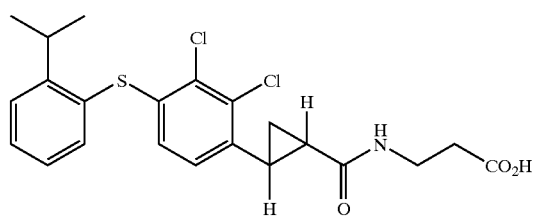

37

The title compound 37 was prepared by the procedures described in Example 2, substituting β-alanine hydrochloride for glycine methyl ester hydrochloride. $^1$H-NMR (CDCl$_3$, 300 MHz) δ7.42 (m, 3H), 7.21 (m, 1H), 6.73 (d, J=8.3 Hz, 1H), 6.40 (d, J=8.3, 1H), 6.27 (t, J=6.1, 1H), 3.59 (m, 2H), 3.46 (m, 1H), 2.64 (m, 3H), 1.61 (m, 1H), 1.40 (m, 1H), 1.23 (m, 1=H), 1.18 (d, J=6.8 Hz, 6H), MS (APCI) (M)$^+$ at m/z 454, 452 Anal. Calc'd for C$_{22}$H$_{23}$NO$_3$SCl$_2$.0.5 H$_2$O: C, 57.27; H, 5.24; N, 3.04. Found: C, 57.22; H, 5.12; N, 2.84.

EXAMPLE 17

(±)-(2-Isopropylphenyl)[2,3-dichloro-4-(trans-(2-(3-carboxypropylamino)carbonyl)cycloprop-1-yl)phenyl] sulfide, 38, was synthesized according to the following procedure.

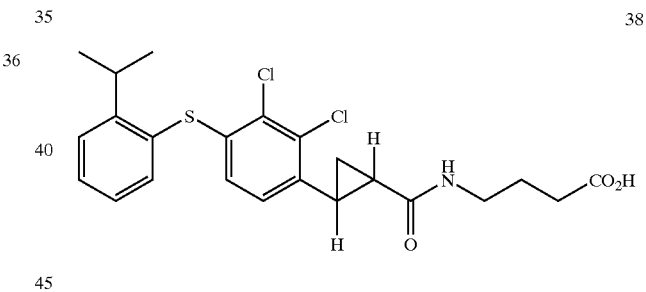

38

The title compound 38 was prepared by the procedure described in Example 2, substituting ethyl 4-amino butyrate for glycine methyl ester hydrochloride. $^1$H-NMR (CDCl$_3$, 300 MHz) δ7.41 (m, 3H), 7.22 (m, 1H), 6.74 (d, J=8.5 Hz, 1H), 6.40 (d, J=8.5, 1H), 5.96 (t, J=6.0, 1H), 3.41 (m, 3H), 2.63 (m, 1H), 2.43 (t, J=7.0 Hz, 2H), 1.88 (m, 2H), 1.61 (m, 1H), 1.39 (m, 1H), 1.22 (m, 1H), 1.18 (d, J=6.8 Hz, 6H), MS (APCI) (M)$^+$ at m/z 468, 466 Anal. Calc'd for C$_{23}$H$_{25}$NO$_3$SCl$_2$.0.1 H$_2$O.0.05 CH$_3$CN: C, 59.00; H, 5.43; N, 3.13. Found: C, 58.98; H, 5.49; N, 3.13.

EXAMPLE 18

(±)-(2-Isopropylphenyl)[2,3-dichloro-4-(trans-(2-(4-carboxypiperidin-1-yl)carbonyl)cycloprop-1-yl)phenyl] sulfide, 39, was synthesized according to the following procedure.

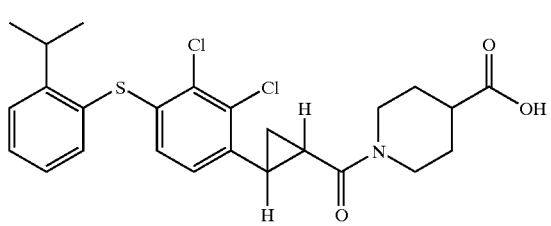

39

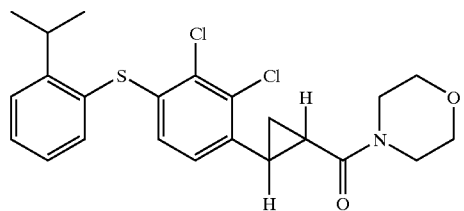

41

The title compound 39 was prepared by the procedure described in Example 3 substituting ethyl isonipecotate for ethyl nipecotate. ¹H-NMR (CDCl₃, 300 MHz)δ7.44 (m, 3H), 7.22 (m, 1H), 6.76 (d, J=8.5 Hz, 1H), 6.40 (d, J=8.5, 1H), 4.45 (m, 1H), 4.03 (m, 1H), 3.47 (m, 1H), 3.23 (m, 1H), 2.91 (m, 1H), 2.61 (m, 2H), 1.95 (m, 3H), 1.64–1.82 (m, 3H), 1.22 (m, 1H), 1.18 (d, J=6.8 Hz, 6H), MS (APCI) (M)⁺ at m/z 494, 492 Anal. Calc'd for C₂₅H₂₇NO₃SCl₂.0.65 H₂O.0.1 TFA: C, 58.71; H, 5.55; N, 2.72. Found: C, 58.7; H, 5.56; N, 2.49.

EXAMPLE 19

(±)-(2-Isopropylphenyl)[2,3-dichloro-4-(trans-(2-(2-carboxypiperidin-1-yl)carbonyl)cycloprop-1-yl)phenyl] sulfide, 40, was synthesized according to the following procedure.

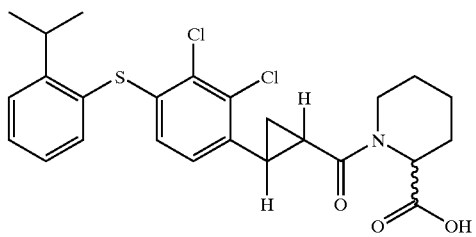

40

The title compound 40 was prepared by the procedure described in Example 3, substituting ethyl pipecolinate for ethyl nipecotate. ¹H-NMR (CDCl₃, 300 MHz) δ7.44 (m, 3H), 7.22 (m, 1H), 6.77 (d, J=8.5 Hz, 1H), 6.40 (d, J=8.5, 1H), 5.28 (m, 1H), 3.98 (m, 1H), 3.47 (m, 1H), 3.31 (m, 1H), 2.58 (m, 1H), 2.28 (m, 1H), 1.56–1.89 (m, 7H), 1.26 (m, 1H), 1.18 (dd, J=6.8, 1.0 Hz, 6H), MS (APCI) (M)⁺ at m/z 494, 492 Anal. Calc'd for C₂₅H₂₇NO₃SCl₂.0.3 H₂O.0.1 TFA: C, 59.43; H, 5.48; N, 2.75. Found: C, 59.41; H, 5.48; N, 2.56.

EXAMPLE 20

(±)-(2-Isopropylphenyl)[2,3-dichloro-4-(trans-(2-(morpholin-1-yl)carbonyl)cycloprop-1-yl)phenyl]sulfide, 41, was synthesized according to the following procedure.

The title compound 41 was prepared by the procedure described in Example 3, substituting morpholine for ethyl nipecototate and omitting the final hydrolysis protocol. ¹H-NMR (CDCl₃, 300 MHz) δ7.43 (m, 3H), 7.22 (m, 1H), 6.77 (d, J=8.5 Hz, 1H), 6.40 (d, J=8.5, 1H), 3.53–3.82 (m, 8H), 3.47 (m, 1H), 2.67 (m, 1H), 1.64 (m, 2H), 1.23 (m, 1H), 1.18 (d, J=6.8 Hz 6H), MS (APCI) (M)⁺ at m/z 452, 450.

EXAMPLE 21

(±)-(2-Isopropylphenyl)[2,3-dichloro-4-(trans-(2-(4-acetylpiperazin-1-yl)carbonyl)cycloprop-1-yl)phenyl] sulfide, 42, was synthesized according to the following procedure.

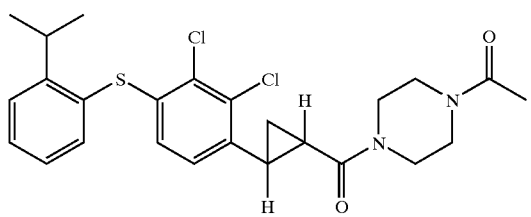

42

The title compound 42 was prepared by the procedure described in Example 3, substituting N-acetylpiperazine for ethyl nipectotate and omitting the final hydrolysis protocol. ¹H-NMR (CDCl₃, 300 MHz) δ7.44 (m, 3H), 7.22 (m, 1H), 6.77 (d, J=8.5 Hz, 1H), 6.40 (d, J=8.5, 1H), 3.42–3.86 (m, 9H), 2.64 (m, 1H), 2.14 (s, 3H), 1.71 (m, 2H), 1.28 (m, 1H), 1.18 (d, J=6.6 Hz, 6H), MS (APCI) (M)⁺ at m/z 493, 491.

EXAMPLE 22

(±)-(2-Isopropylphenyl)[2,3-dichloro-4-(trans-(2-((3-(1-pyrrolidin-2-onyl)-prop-1-ylamino)carbonyl)cycloprop-1-yl)phenyl]sulfide, 43, was synthesized according to the following procedure.

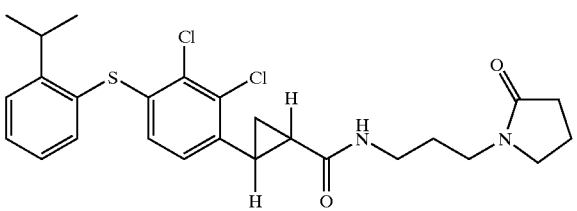

43

The title compound 43 was prepared by the procedure described in Example 3, substituting 3-aminopropyl-2-pyrrolidinone for ethyl nipectotate and omitting the final hydrolysis protocol. ¹H-NMR (CDCl₃, 300 MHz) δ7.43 (m, 3H), 7.22 (m, 1H), 7.05 (t, J=6.8, 1H), 6.72 (d, J=8.5 Hz, 1H), 6.40 (d, J=8.5, 1H). 3.28–3.50 (m, 6H), 3.28 (m, 1H), 2.67 (m, 1H), 2.41 (t, J=8.1 Hz, 2H), 2.07 (m, 2H), 1.70 (m, 2H), 1.55 (m, 2H), 1.18 (d, J=6.8 Hz, 6H), 1.14 (m, 1H), MS (APCI) (M)⁺ at m/z 507, 505.

EXAMPLE 23

(±)-(2-Isopropylphenyl)[2,3-dichloro-4-(trans-(2-(pyrrolidin-1-yl)carbonyl)cycloprop-1-yl)phenyl]sulfide, 44, was synthesized according to the following procedure.

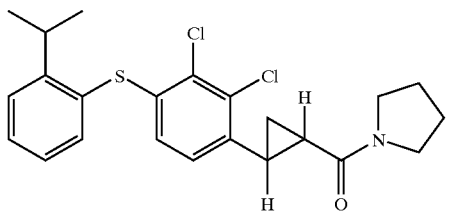

44

The title compound 44 was prepared by the procedure described in Example 3, substituting pyrrolidine for ethyl nipectotate and omitting the final hydrolysis protocol. ¹H-NMR (CDCl₃, 300 MHz) δ7.43 (m, 3H), 7.22 (m, 1H), 6.77 (d, J=8.5 Hz, 1H), 6.40 (d, J=8.5, 1H), 3.41–3.68 (m, 5H), 2.62 (m, 1H), 1.92 (m, 4H), 1.67 (m, 2H), 1.18 (d, J=6.8 Hz, 7H), MS (APCI) (M)⁺ at m/z 436, 434.

EXAMPLE 24

(±)-(2-Isopropylphenyl)[2,3-dichloro-4-(trans-2-(cyclobutylaminocarbonyl)cycloprop-1-yl)phenyl]sulfide, 45, was synthesized according to the following procedure.

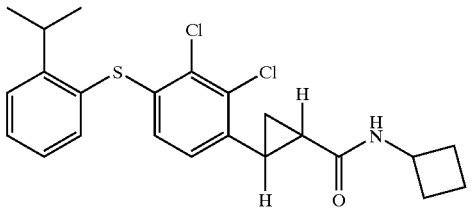

45

The title compound 45 was prepared by the procedure described in Example 3 substituting cyclobutylamine for ethyl nipectotate and omitting the final hydrolysis protocol. ¹H-NMR (CDCl₃, 300 MHz) δ7.43 (m, 3H), 7.22 (m, 1H), 6.72 (d, J=8.5 Hz, 1H), 6.40 (d, J=8.5, 1H), 5.77 (d, J=8.1, 1H), 4.48 (m, 1H), 3.46 (m, 1H), 2.62 (m, 1H), 2.36 (m, 2H), 1.86 (m, 2H), 1.71 (m, 2H), 1.55 (m, 1H), 1.34 (m, 1H), 1.18 (d, J=6.8 Hz, 6H), MS (APCI) (M)⁺ at m/z 436, 434.

EXAMPLE 25

(±)-(2-Isopropylphenyl)[2,3-dichloro-4-(trans-(2-(azetidin-1-yl)carbonyl)cycloprop-1-yl)phenyl]sulfide, 46, was synthesized according to the following procedure.

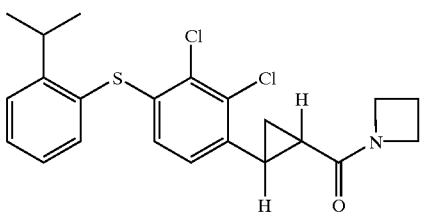

46

The title compound 46 was prepared by the procedure described in Example 3 substituting azetidine for ethyl nipectotate and omitting the final hydrolysis protocol. ¹H-NMR (CDCl₃, 300 MHz) δ7.43 (m, 2H), 7.22 (m, 2H), 6.75 (d, J=8.5 Hz, 1H), 6.40 (d, J=8.5, 1H), 4.00–4.30 (m, 4H), 3.47 (m, 1H), 2.58 (m, 1H), 2.32 (m, 2H), 1.60 (m, 2H), 1.45 (m, 1H), 1.19 (d, J=6.8 Hz, 6H), MS (APCI) (M)⁺ at m/z 422, 420.

EXAMPLE 26

(±)-( 2-Isopropylphenyl)[2,3-dichloro-4-(trans-(2-(2-morpholin-1-ylethyl)carbonyl)cycloprop-1-yl)phenyl]sulfide, 47, was synthesized according to the following procedure.

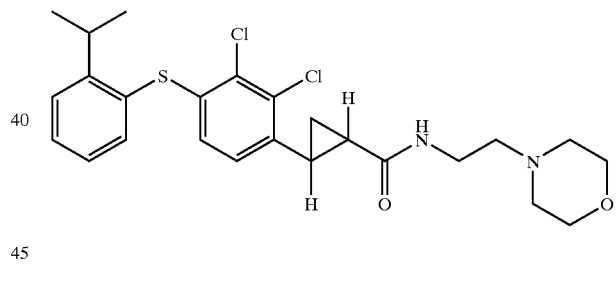

47

The title compound 47 was prepared by the procedure described in EXAMPLE 3 substituting 4-(2-aminoethyl)morpholine for ethyl nipectotate and omitting the final hydrolysis protocol. ¹H-NMR (CDCl₃, 300 MHz) δ7.43 (m, 3H), 7.22 (m, 1H), 7.19 (m, 1H), 6.74 (d, J=8.5 Hz, 1H), 6.40 (d, J=8.5, 1H), 3.76 (m, 4H), 3.46 (m, 3H), 2.53 (m, 7H), 1.62 (m, 1H), 1.49 (m, 1H), 1.18 (d, J=6.8 Hz, 7H), MS (APCI) (M)⁺ at m/z 495, 493.

EXAMPLE 27

(2-(3-Carboxypiperidin-1-yl)phenyl)[2-trifluoromethyl-4-(trans-(2-((3-(1-pyrrolidin-2-onyl)-prop-1-ylamino)carbonyl)cycloprop-1-yl)phenyl]sulfide; Isomer #1, 48A, was synthesized according to the following procedure.

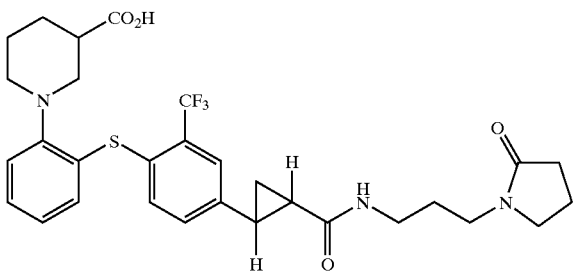

48

The title compound 48A was prepared by the procedure described in Example 7, substituting compound 19a for compound 19 and ethyl nipecotate for morpholine. The crude products were dissolved in THF (1.0 mL) and EtOH (1.0 mL) and treated with 2N NaOH until ester hydrolysis was complete by TLC. The solution was poured into 2N HCl and extracted with EtOAc (2×). The combined organic layers were rinsed with brine, dried over $Na_2SO_4$, concentrated, and purified by preparative HPLC. $^1$H-NMR ($CDCl_3$, 300 MHz) δ7.20–7.52 (m, 5H), 6.79–6.91 (m, 2H), 4.00 (br s, 2H), 2.90–3.65 (m, 10H), 2.50 (m, 4H), 2.13 (m, 3H), 1.50–2.02 (m, 6H), 1.45 (m, 1H), 1.34 (m, 1H); MS (APCI) (M+H)$^+$ at m/z 590.

EXAMPLE 28

(2-(3-Carboxypiperidin-1-yl)phenyl)[2-trifluoromethyl-4-(trans-(2-((3-(1-pyrrolidin -2-onyl)-prop-1-ylamino) carbonyl)cycloprop-1-yl)phenyl]sulfide; Isomer #2, 48B, was synthesized according to the following procedure. The title compound 48B was prepared by the procedure described in Example 7, substituting compound 19B for compound 19 and ethyl nipecotate for morpholine. The crude products were dissolved in THF (1.0 mL) and EtOH (1.0 mL) and treated with 2N NaOH until ester hydrolysis was complete by TLC. The solution was poured into 2N HCl and extracted with EtOAc (2×). The combined organic layers were rinsed with brine, dried over $Na_2SO_4$, concentrated, and purified by preparative HPLC. $^1$H-NMR ($CDCl_3$, 300 MHz) δ7.20–7.52 (m, 5H), 6.79–6.91 (m, 2H), 4.00 (br s, 2H), 2.90–3.65 (m, 10H), 2.50 (m, 4H), 2.13 (m, 3H), 1.50–2.02 (m, 6H), 1.45 (m, 1H), 1.34 (m, 1H); MS (APCI) (M+H)$^+$ at m/z 590; Anal. Calc'd for $C_{30}H_{34}N_3O_4SF_3$·0.4 $H_2O$·0.75 TFA: C, 55.44; H, 5.25; N, 6.16. Found: C, 55.42; H, 5.26; N, 6.09.

EXAMPLE 29

(2-(Morpholin-1-yl)phenyl)[2-trifluoromethyl-4-(trans-(2-((3-(1-pyrrolidin-2-onyl)-prop-1-ylamino)carbonyl) cycloprop-1-yl)phenyl]sulfide; Isomer #1, 28A, was synthesized according to the following procedure. The title compound 28A was prepared by the procedure described in Example 7, substituting compound 19A for compound 19. $^1$H NMR (300 MHz, $CDCl_3$) δ7.45 (d, J=1.8 Hz, 1H), 7.07–7.24 (m, 4H), 6.97 (dt, J=7.5, 1.5 Hz, 1H), 6.84 (dd, J=8.1, 1.5 Hz, 1H), 3.78 (t, J=4.6 Hz, 4H), 3.42 (m, 4H), 3.17–3.37 (m, 4H), 3.05 (t, J=4.4 Hz, 4H), 2.53 (m, 1H), 2.47 (m, 2H), 2.09 (m, 2H), 1.72 (m, 3H), 1.25 (m, 1H); MS (APCI) (M+H)$^+$ at m/z=548; FAB HRMS m/z (calc'd for $C_{28}H_{33}N_3O_3S_1F_3$ (M+H)=548.2195 Obs 548.2188); Anal. Calc'd for $C_{28}H_{32}N_3O_3SF_3$·2.55 $H_2O$: C, 56.66; H, 6.30; N, 7.08. Found: C, 56.7; H, 6.01; N, 6.72.

EXAMPLE 30

(2-(Morpholin-1-yl)phenyl)[2-trifluoromethyl-4-(trans-(2-((3-(1-pyrrolidin-2-onyl)-prop-1-ylamino)carbonyl) cycloprop-1-yl)phenyl]sulfide; Isomer #2, 28B, was synthesized by the following procedure. The title compound 28B was prepared by the procedure described in Example 7, substituting compound 19B for compound 19. $^1$H NMR (300 MHz, $CDCl_3$) δ7.45 (d, J=1.8 Hz, 1H), 7.07–7.24 (m, 4H), 6.97 (dt, J=7.5, 1.5 Hz, 1H), 6.84 (dd, J=8.1, 1.5 Hz, 1H), 3.78 (t, J=4.6 Hz, 4H), 3.42 (m, 2H), 3.17–3.37 (m, 4H), 3.05 (t, J=4.4 Hz, 4H), 2.53 (m, 1H), 2.47 (m, 2H), 2.09 (m, 2H), 1.72 (m, 3H), 1.25 (m, 1H); MS (APCI) (M+)$^+$ at m/z=548; Anal. Calc'd for $C_{28}H_{32}N_3O_3SF_3$·0.55 $H_2O$·0.3 TFA: C, 58.05; H, 5.69; N, 7.10. Found: C, 58.1; H, 5.67; N, 7.04.

EXAMPLE 31

(2-(3-Carboxypiperidin-1-yl)phenyl)[2,3-dichloro-4-(trans-(2-((3-(-1-pyrrolidin-2-onyl)-prop-1-ylamino) carbonyl)cycloprop-1-yl)phenyl]sulfide; Isomer #2, 49B, was synthesized according to the following procedure.

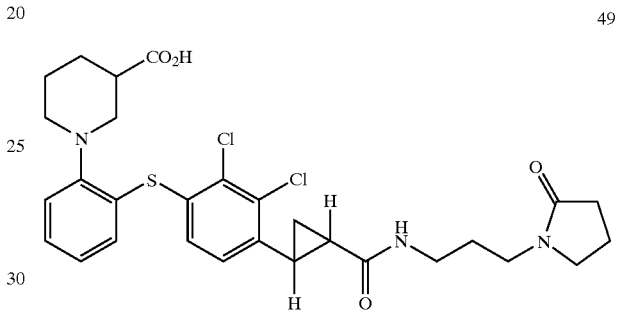

49

31A. Resolution of compound 35 using a Chiralpak AD HPLC column eluting with 85:15 hexane:EtOH gave baseline resolution of two enantiomers which were both >98% ee by HPLC. The earlier eluting isomer is denoted isomer #1, 35A and the later eluting isomer is denoted isomer #2, 35B.

31B. The title compound 49B was prepared by the procedure described in Example 7, substituting isomer #2, 35B for compound 19 and ethyl nipecotate for morpholine. The crude products were dissolved in THF (1.0 mL) and EtOH (1.0 mL) and treated with 2N NaOH until ester hydrolysis was complete by TLC. The solution was poured into 2N HCl and extracted with EtOAc (2×). The combined organic layers were rinsed with brine, dried over $Na_2SO_4$, concentrated, and purified by preparative HPLC. $^1$H-NMR ($CDCl_3$, 300 MHz) δ7.55 (m, 1H), 7.40 (m, 1H), 7.28 (m, 2H), 6.81 (d, J=8.5 Hz, 1H), 6.60 (s, 1H), 6.57 (d, J=8.5 Hz, 1H), 3.00–3.60 (m, 8H), 2.45–2.93 (m, 5H), 1.25–2.17 (m, 12H), MS (APCI) (M)$^+$ at m/z 590; Anal. Calc'd for $C_{29}H_{33}N_3O_4SCl_2$·0.25 $H_2O$·2.05 TFA: C, 47.97; H, 4.32; N, 5.07. Found. C, 47.96; H, 4.33; N, 5.08.

EXAMPLE 32

(2-(3-Carboxypiperidin-1-yl)phenyl)[2,3-dichloro-4-(trans-(2-((3-(1-pyrrolidin-2-onyl)-prop-1-ylamino) carbonyl)cycloprop-1-yl)phenyl]sulfide; Isomer #1, 49A, was synthesized according to the following procedure.

32A. Isomer #1, 35A. was also isolated from the procedure described in Example 31, step A.

32B. The title compound 49A was prepared by the procedure described in Example 7, substituting compound 35A for compound 19 and ethyl nipecotate for morpholine. The crude products were dissolved in THF (1.0 mL) and EtOH (1.0 mL) and treated with 2N NaOH until ester hydrolysis was complete by TLC. The solution was poured into 2N HCl and extracted with EtOAc (2×). The combined organic layers were rinsed with brine, dried over Na$_2$SO$_4$, concentrated, and purified by preparative HPLC. $^1$H-NMR (CDCl$_3$, 300 MHz) δ7.78 (m, 1H), 7.64 (m, 1H), 7.49 (m, 1H), 7.42 (m, 1H), 7.24 (m, 1H), 6.81 (br s, 1H), 6.77 (m, 1H), 6.40 (m, 1H), 3.70 (m, 1H), 3.48 (m, 5H), 3.30 (m, 1H), 3.18 (m, 1H), 2.62–3.08 (m, 4H), 2.52 (m, 3H), 2.11 (m, 3H), 1.55–1.90 (m, 5H), 1.25–1.45 (m, 2H); MS (APCI) (M)$^+$ at m/z 590; Anal. Calc'd for C$_{29}$H$_{33}$N$_3$O$_4$SCl$_2$.0.7H$_2$O.2.15 TFA: C, 47.15; H, 4.34; N, 4.95. Found: C, 47.11; H, 4.25; N, 5.3.

EXAMPLE 33

(2-Methoxyphenyl)[2,3-dichloro-4-(trans-2-(carboxymethylamino)carbonyl)cycloprop-1-yl)phenyl]sulfide, Isomer #1, 50A, was synthesized according to the following procedure.

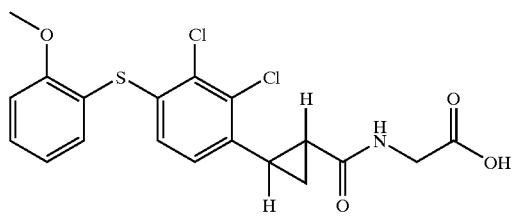

50

33A. First, (±)-(2-Methoxyphenyl)[2,3-dichloro-4-(trans-2-ethoxycarbonyl)cycloprop-1-yl)phenyl]sulfide, 51, was synthesized according to the following procedure.

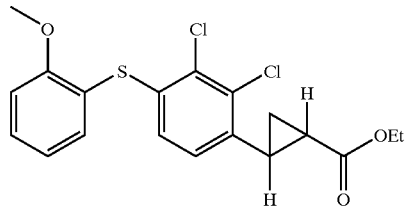

51

Compound 51 was prepared according to the procedures of Example 2A and 2B, substituting 2-methoxythiophenol for 2-isopropylthiophenol and eliminating the final hydrolysis procedure.

33B. Then (2-methoxyphenyl)[2,3-dichloro-4-(trans-2-ethoxycarbonyl)cycloprop-1-yl)phenyl]sulfide, Isomer # 1, 51A, was prepared as follows. Resolution of compound 51 using a Chiralcel OD HPLC column eluting with 95:5 hexane:i-PrOH gave baseline resolution of two enantiomers which were both >98% ee by HPLC. The earlier eluting isomer is denoted isomer #1 (51A) and the later eluting isomer is denoted isomer #2 (15B).

33C. The title compound 50A was prepared from compound 51A using the hydrolysis procedure described in Example 1C followed by the coupling procedure described in Example 3, substituting glycine methyl ester hydrochloride for ethyl nipecotate. $^1$H NMR (CDCl$_3$, 300 MHz) 7.45–7.30 (m, 2H), 6.98 (m, 2H), 6.77 (d, J=9 Hz, 1H), 6.61 (d, J=9 Hz, 1H), 6.33 (m, 1H), 4.14 (m, 2H), 3.82 (s, 3H), 2.67 (m, 1H), 1.62 (m, 1H), 1.54 (m, 1H), 1.27 (m, 1H); MS (APCI) (M)$^+$ at m/z 426; Anal. Calcd for C$_{19}$H$_{17}$NO$_4$SCl$_2$.0.4H$_2$O.0.1 TFA: C, 51.83; H, 4.06; N, 3.15. Found: C, 51.82; H, 4.05; N, 3.06.

EXAMPLE 34

(2-Methoxyphenyl)[2,3-dichloro-4-(trans-2-(2-carboxyethylamino)carbonyl)cycloprop-1-yl)phenyl]sulfide, Isomer #1, 52A, was synthesized according to the following procedure.

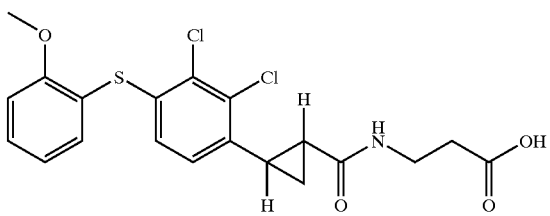

52

The title compound 52A was prepared by the procedures described in Example 33, substituting β-alanine ethyl ester for glycine methyl ester hydrochloride. $^1$H NMR (CDCl3, 300 MHz) 7.45–7.30 (m, 2H), 6.97 (m, 2H), 6.77 (d, J=9 Hz,1H), 6.60 (d, J=9 Hz, 1H), 6.32 (m, 1H), 3.82 (s, 3H), 3.61 (m, 2H), 2.65 (m, 3H), 1.62 (m, 1H), 1.42 (m, 1H), 1.22 (m, 1H); MS (APCI) (M)$^+$ at m/z 440; Anal. Calc'd for C$_{29}$H$_{33}$N$_3$O$_4$SCl$_2$.0.25 H$_2$O.2.05 TFA: C, 47.97; H, 4.32; N, 5.07. Found: C, 47.96; H, 4.33; N, 5.08.

EXAMPLE 35

(2-Methoxyphenyl)[2,3-dichloro-4-(trans-2-(3-carboxypropylamino)carbonyl)cycloprop-1-yl)phenyl]sulfide, Isomer #1, 53A, was synthesized according to the following procedure.

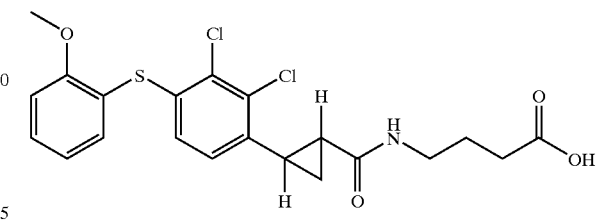

53

The title compound 53A was prepared by the procedure described in Example 33, substituting ethyl 4-aminobutyrate for glycine methyl ester hydrochloride. $^1$H NMR (CDCl$_3$, 300 MHz) 7.45–7.30 (m, 2H), 6.98 (m, 2H), 6.78 (d, J=9 Hz,1H), 6.61 (d, J=9 Hz, 1H), 6.00 (m, 1H), 3.83 (s, 3H), 3.41 (m, 2H), 2.64 (m, 1H), 2.43 (t, J=8 Hz, 2H), 1.88 (m, 2H), 1.62 (m, 1H), 1.41 (m, 1H), 1.23 (m, 1H); MS (APCI) (M)$^+$ at m/z 454; Anal. Calc'd for C$_{23}$H$_{23}$NO$_4$SCl$_2$.0.7 H$_2$O.0.9 TFA: C, 50.01; H, 4.28; N, 2.35. Found: C, 50; H, 4.3; N, 2.46.

EXAMPLE 36

(2-Methoxyphenyl)[2,3-dichloro-4-(trans-2-(4-carboxypiperidin-1-yl)carbonyl)cycloprop-1-yl)phenyl]sulfide, Isomer #1, 54A, was synthesized according to the following procedure.

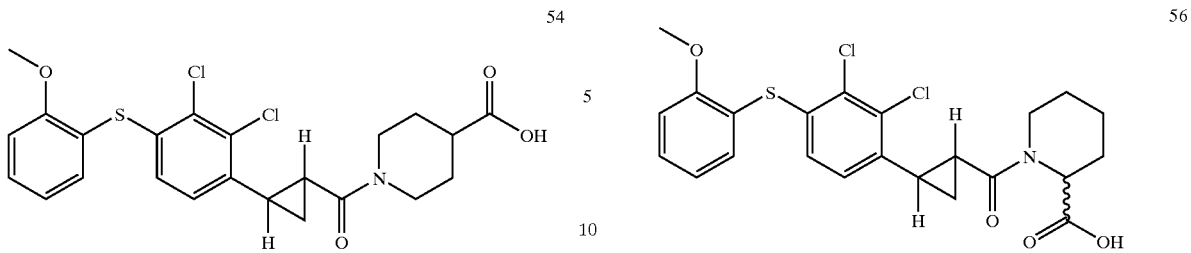

The title compound 54A was prepared by the procedure described in Example 33, substituting ethyl isonipecotate for glycine methyl ester hydrochloride. $^1$H NMR (CDCl$_3$, 300 MHz) 7.45–7.30 (m, 2H), 6.98 (m, 2H), 6.79 (d, J=9 Hz,1H), 6.62 (d, J=9 Hz, 1H), 4.46 (m, 1H), 4.05 (m, 1H), 3.83 (s, 3H), 3.25 (m, 1H), 2.96 (m, 1H), 2.62 (m, 2H), 2.00 (m, 2H), 1.81 (m, 2H), 1.72 (m, 2H), 1.24 (m, 1H); MS (APCI) (M)$^+$ at m/z 482, 480; Anal. Calc'd for C$_{23}$H$_{23}$NO$_4$SCl$_2$.0.7 H$_2$O.0.9 TFA: C, 50.01; H, 4.28; N, 2.35. Found: C, 50; H, 4.3; N, 2.46.

EXAMPLE 37

(2-Methoxyphenyl)[2,3-dichloro-4-(trans-2-(3-carboxypiperidin-1-yl)carbonyl)cycloprop-1-yl)phenyl] sulfide, Isomer #1, 55A, was synthesized according to the following procedure.

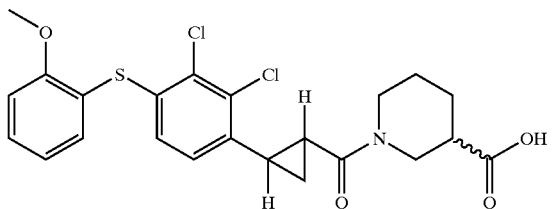

The title compound 55A was prepared by the procedure described in Example 33, substituting ethyl nipecotate for glycine methyl ester hydrochloride. $^1$H NMR (CDCl$_3$, 300 MHz) 7.45–7.30 (m, 2H), 6.98 (m, 2H), 6.79 (d, J=9 Hz,1H), 6.62 (d, J=9 Hz, 1H), 4.51 (m, 1H), 4.07 (m, 1H), 3.83 (s, 3H), 3.50–3.00 (m, 2H), 2.62 (m, 2H), 2.20–1.40 (m, 6H), 1.24 (m, 1H); MS (APCI) (M)$^+$ at m/z 482, 480; Anal. Calc'd for C$_{23}$H$_{23}$NO$_4$SCl$_2$.0.7 H$_2$O.0.9 TFA: C, 50.01; H, 4.28; N, 2.35. Found: C, 50; H, 4.3; N, 2.46.

EXAMPLE 38

(2-Methoxyphenyl)[2,3-dichloro-4-(trans-2-(2-carboxypiperidin-1-yl)carbonyl)cycloprop-1-yl)phenyl] sulfide, Isomer #1, 56A, was synthesized according to the following procedure.

The title compound 56A was prepared by the procedures described in Example 33, substituting ethyl pipecolinate for glycine methyl ester hydrochloride. $^1$H NMR (CDCl$_3$, 300 MHz) 7.45–7.30 (m, 2H), 6.99 (m, 2H), 6.81 (d, J=9 Hz,1H), 6.61 (d, J=9 Hz, 1H), 5.38 (m, 1H), 4.04 (m, 1H), 3.84 (s, 3H), 3.50 (s, 1H), 3.31 (m, 1H), 2.70 (m, 1H), 2.62 (m, 1H), 1.89 (m, 1H), 1.72 (m, 4H), 1.62 (m, 2H), 1.31 (m, 1H); (MS (APCI) (M)$^+$ at m/z 482, 480; Anal. Calc'd for C$_{23}$H$_{23}$NO$_4$SCl$_2$.1.5 H$_2$O.1.25 TFA: C, 47.12; H, 4.23; N, 2.15. Found: C, 47.11; H, 4.16; N, 2.49.

EXAMPLE 39

(2-Methoxyphenyl)[2,3-dichloro-4-(trans-2-(carboxymethylamino)carbonyl)cycloprop-1-yl)phenyl] sulfide, Isomer #2, 50B, was synthesized according to the following procedure.

39A. First, (2-Methoxyphenyl)[2,3-dichloro-4-(trans-2-ethoxycarbonyl)cycloprop-1-yl)phenyl]sulfide, Isomer #2, 51B, was also isolated from the procedure described in Example 33B.

39B. The title compound 50B was prepared from compound 51B using the hydrolysis procedure described in Example 1, step C followed by the coupling procedure described in Example 3, substituting glycine methyl ester hydrochloride for ethyl nipecotate. $^1$H NMR (CDCl$_3$, 300 MHz) 7.45–7.30 (m, 2H), 6.98 (m, 2H), 6.77 (d, J=9 Hz, 1H), 6.61 (d, J=9 Hz, 1H), 6.33 (m, 1H), 4.14 (m, 2H), 3.82 (s, 3H), 2.67 (m, 1H), 1.62 (m, 1H), 1.54 (m, 1H), 1.27 (m, 1H). m/e (ESI) 424, 426 (MH$^-$) Anal. Calc'd for C$_{19}$H$_{17}$C$_{12}$NO$_4$S.0.40 H$_2$O: C, 52.64; H, 4.14; N, 3.23. Found: C, 52.59; H, 4.01; N, 3.40.

EXAMPLE 40

(2-Methoxyphenyl)[2,3-dichloro-4-(trans-2-(2-carboxyethylamino)carbonyl)cycloprop-1-yl)phenyl] sulfide, Isomer #2, 52B, was synthesized according to the following procedure.

The title compound 52B was prepared by the procedures described in Example 39, substituting β-alanine ethyl ester for glycine methyl ester hydrochloride. $^1$H NMR (CDCl$_3$, 300 MHz) 7.45–7.30 (m, 2H), 6.97 (m, 2H), 6.77 (d, J=9 Hz,1H), 6.60 (d, J=9 Hz, 1H), 6.32 (m, 1H), 3.82 (s, 3H), 3.61 (m, 2H), 2.65 (m, 3H), 1.62 (m, 1H), 1.42 (m, 1H), 1.22 (m, 1H). m/e (ESI) 438, 440 (MH$^-$) Anal. Calc'd for C$_{20}$H$_{19}$C$_{12}$NO$_4$S.0.45 H$_2$O: C, 53.57; H, 4.47; N, 3.12. Found: C, 53.53; H, 4.42 N, 3.00.

EXAMPLE 41

(2-Methoxyphenyl)[2,3-dichloro-4-(trans-2-(3-carboxypropylamino)carbonyl)cycloprop-1-yl)phenyl] sulfide, Isomer #2, 53B, was synthesized according to the following procedure.

The title compound 53B was prepared by the procedures described in Example 39, substituting ethyl 4-aminobutyrate for glycine methyl ester hydrochloride. 1H NMR (CDCl$_3$, 300 MHz) 7.45–7.30 (m, 2H), 6.98 (m, 2H), 6.78 (d, J=9 Hz, 1H), 6.61 (d, J=9 Hz, 1H), 6.00 (m, 1H), 3.83 (s, 3H), 3.41 (m, 2H), 2.64 (m, 1H), 2.43 (t, J=8 Hz, 2H), 1.88 (m, 2H), 1.62 (m, 1H), 1.41 (m, 1H), 1.23 (m, 1H). m/e (ESI) 452, 454 (MH$^-$) Anal. Calc'd for C$_{21}$H$_{21}$Cl$_2$NO$_4$S.0.55 H$_2$O 0: C, 54.33; H, 4.80; N, 3.02. Found: C, 54.31; H, 4.65; N, 2.76.

EXAMPLE 42

(2-Methoxyphenyl)[2,3-dichloro-4-(trans-2-(4-carboxypiperidin-1-yl)carbonyl)cycloprop-1-yl)phenyl] sulfide, Isomer #2, 54B, was synthesized according to the following procedure.

The title compound 54B was prepared by the procedure described in Example 39, substituting ethyl isonipecotate for glycine methyl ester hydrochloride. 1H NMR (CDCl$_3$, 300 MHz) 7.45–7.30 (m, 2H), 6.98 (m, 2H), 6.79 (d, J=9 Hz, 1H), 6.62 (d, J=9 Hz, 1H), 4.46 (m, 1H), 4.05 (m, 1H), 3.83 (s, 3H), 3.25 (m, 1H), 2.96 (m, 1H), 2.62 (m, 2H), 2.00 (m, 2H), 1.81 (m, 2H), 1.72 (m, 2H), 1.24 (m, 1H). m/e (ESI) 478, 480 (MH$^-$) Anal. Calc'd for C$_{23}$H$_{23}$Cl$_2$NO$_4$S: C, 57.50; H, 4.83; N, 2.92. Found: C, 57.33; H, 4.82; N, 2.64.

EXAMPLE 43

(2-Methoxyphenyl)[2,3-dichloro-4-(trans-2-(3-carboxypiperidin-1-yl)carbonyl)cycloprop-1-yl)phenyl] sulfide, Isomer #2, 55B, was synthesized according to the following procedure.

The title compound 55B was prepared by the procedure described in Example 39, substituting ethyl nipecotate for glycine methyl ester hydrochloride. $^1$H NMR (CDCl$_3$, 300 MHz) 7.45–7.30 (m, 2H), 6.98 (m, 2H), 6.79 (d, J=9 Hz,1H), 6.62 (d, J=9 Hz, 1H), 4.51 (m, 1H), 4.07 (m, 1H), 3.83 (s, 3H), 3.50–3.00 (m, 2H), 2.6 (m, 2H), 2.20–1.40 (m, 6H), 1.24 (m, 1H). m/e (ESI) 478, 480 (MH$^-$) Anal. Calc'd for C$_{23}$H$_{23}$Cl$_2$NO$_4$S.0.25 H$_2$O: C, 56.97; H, 4.88; N, 2.89. Found: C, 56.91; H, 4.68N, 2.68.

EXAMPLE 44

(2-Methoxyphenyl)[2,3-dichloro-4-(trans-2-(2-carboxypiperidin-1-yl)carbonyl)cycloprop-1-yl)phenyl] sulfide, Isomer #2, 56B, was synthesized according to the following procedure.

The title compound 56B was prepared by the procedure described in Example 39, substituting ethyl pipecolinate for glycine methyl ester hydrochloride. $^1$H NMR (CDCl$_3$, 300 MHz) 7.45–7.30 (m, 2H), 6.99 (m, 2H), 6.81 (d, J=9 Hz,1H), 6.61 (d, J=9 Hz, 1H), 5.38 (m, 1H), 4.04 (m, 1H), 3.84 (s, 3H), 3.50 (s, 1H), 3.31 (m, 1H), 2.70 (m, 1H), 2.62 (m, 1H), 1.89 (m, 1H), 1.72 (m, 4H), 1.62 (m, 2H), 1.31 (m, 1H). m/e (ESI) 478, 480 (MH$^-$) Anal. Calc'd for C$_{23}$H$_{23}$Cl$_2$NO$_4$S.0.40 CH$_2$Cl$_2$: C, 54.64; H, 4.66; N, 2.72. Found: C, 54.77; H, 4.61; N, 2.53.

EXAMPLE 45

(2-Methoxyphenyl)[2,3-dichloro-4-(trans-(2-((3-(1-pyrrolidin-2-onyl)-prop-1-ylamino)carbonyl)cycloprop-1-yl)phenyl]sulfide, Isomer #2, 57B, was synthesized as follows.

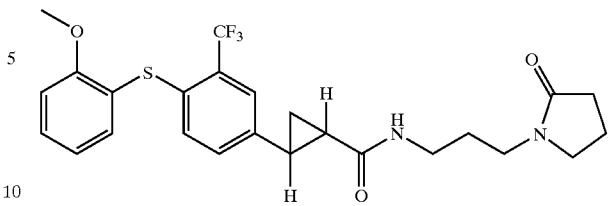

57

The title compound 57B was prepared by the procedure described in Example 39, substituting pyrrolidone-3-propylamine for glycine methyl ester hydrochloride, and eliminating the final hydrolysis procedure. $^1$H NMR (CDCl$_3$, 300 MHz) 7.45–7.30 (m, 2H), 7.02 (m, 1H), 6.98 (m, 2H), 6.77 (d, J=9 Hz,1H), 6.63 (d, J=9 Hz, 1H), 3.84 (s, 3H), 3.50–3.25 (m, 5H), 3.20 (m, 1H), 2.67 (m, 1H), 2.42 (t, J=8 Hz, 2H), 2.08 (m, 2H), 1.71 (m, 2H), 1.58 (m, 2H), 1.17 (m, 1H). m/e (ESI) 493, 495 (MH$^+$) Anal. Calc'd for C$_{24}$H$_{26}$Cl$_2$N$_2$O$_3$S.0.40 CH$_2$Cl$_2$: C, 55.57; H, 5.12; N, 5.31. Found: C, 55.65; H, 5.09; N, 5.23.

EXAMPLE 46

Compounds that antagonize the interaction between ICAM-1 and LFA-1 can be identified, and their activities quantitated, using both biochemical and cell-based adhesion assays. A primary biochemical assay, described below as assay 46A, was utilized to measure the ability of the present compounds to block the interaction between the integrin LFA-1 and its adhesion partner ICAM-1.

46A. ICAM-1/LFA-1 Biochemical Interaction Assay

In the biochemical assay, 100 mL of anti-LFA-1 antibody (ICOS Corporation) at a concentration of 5 mg/ml in Dulbecco's phosphate-buffered saline (D-PBS) is used to coat wells of a 96-well microtiter plate overnight at 4° C. The wells are then washed twice with wash buffer (D-PBS w/o Ca$^{++}$ or Mg$^{++}$, 0.05% Tween 20) and blocked by addition of 200 mL of D-PBS, 5% fish skin gelatin. Recombinant LFA-1 (100 mL of 0.7 mg/ml, ICOS Corporation) in D-PBS is then added to each well. Incubation continues for 1 hour at room temperature and the wells are washed twice with wash buffer. Serial dilutions of compounds being assayed as ICAM-1/LFA-1 antagonists, prepared as 10 mM stock solutions in dimethyl sulfoxide (DMSO), are diluted in D-PBS, 2 mM MgCl$_2$, 1% fish skin gelatin and 50 mL of each dilution added to duplicate wells. This is followed by addition of 50 mL of 0.8 mg/ml biotinylated recombinant ICAM-1/Ig (ICOS Corporation) to the wells and the plates are incubated at room temperature for 1 hour The wells are then washed twice with wash buffer and 100 mL of Europium-labeled Streptavidin (Wallac Oy) diluted 1:100 in Delfia assay buffer (Wallac Oy) are added to the wells. Incubation proceeds for 1 hour at room temperature. The wells are washed eight times with wash buffer and 100 μL of enhancement solution (Wallac Oy, cat. No. 1244-105) are added to each well. Incubation proceeds for 5 minutes with constant mixing. Time-resolved fluorimetry measurements are made using the Victor 1420 Multilabel Counter (Wallac Oy) and the percent inhibition of each candidate compound is calculated using the following equation:

$$\% \text{ inhibition} = 100 \times \left\{ 1 - \frac{\text{average OD w/ compound minus background}}{\text{average OD w/o compound minus background}} \right\}$$

where "background" refers to wells that are not coated with anti-LFA-1 antibody.

Compounds of the present invention exhibit inhibitory activity in the above assay as illustrated in Table 1.

TABLE 1

| Compound of Example | % inhibition |
|---|---|
| 1 | 92% @ 4 µM |
| 2 | 95% @ 2 µM |
| 3 | 96% @ 2 µM |
| 4 | 81% @ 2 µM |
| 5 | 94% @ 2 µM |
| 6 | 90% @ 4 µM |
| 7 | 93% @ 4 µM |
| 8 | 94% @ 4 µM |
| 9 | 95% @ 4 µM |
| 10 | 94% @ 4 µM |
| 11 | 44% @ 4 µM |
| 12 | 91% @ 4 µM |
| 13 | 93% @ 4 µM |
| 14 | 92% @ 4 µM |
| 15 | 88% @ 4 µM |
| 16 | 96% @ 2 µM |
| 17 | 95% @ 2 µM |
| 18 | 93% @ 2 µM |
| 19 | 96% @ 2 µM |
| 20 | 96% @ 2 µM |
| 21 | 94% @ 2 µM |
| 22 | 96% @ 2 µM |
| 23 | 94% @ 2 µM |
| 24 | 94% @ 2 µM |
| 25 | 95% @ 2 µM |
| 26 | 95% @ 2 µM |
| 27 | 93% @ 2 µM |
| 28 | 97% @ 2 µM |
| 29 | 94% @ 2 µM |
| 30 | 97% @ 2 µM |
| 31 | 95% @ 4 µM |
| [001b]32 | 96% @ 4 µM |
| 33 | 93% @ 4 µM |
| 34 | 95% @ 4 µM |
| 35 | 95% @ 4 µM |
| 36 | 95% @ 4 µM |
| 38 | 93% @ 4 µM |
| 39 | 94% @ 4 µM |
| 40 | 96% @ 4 µM |
| 41 | 96% @ 4 µM |
| 42 | 96% @ 4 µM |
| 43 | 96% @ 4 µM |
| 45 | 96% @ 4 µM |

Biologically relevant activity of the compounds in this invention was confirmed using a cell-based adhesion assay, (described below as assay 46B) which measured the ability of the present compounds to block the adherence of JY-8 cells (a human EBV-transformed B cell line expressing LFA-1 on its surface) to immobilized ICAM-1.

46B. ICAM-1 /JY-8 Cell Adhesion Assay

For measurement of inhibitory activity in the cell-based adhesion assay, 96-well microtiter plates are coated with 70 µL of recombinant ICAM-1/g (ICOS Corporation) at a concentration of 5 µg/mL in D-PBS w/o $Ca^{++}$ or $Mg^{++}$ overnight at 4° C. The wells are then washed twice with D-PBS and blocked by addition of 200 µL of D-PBS, 5% fish skin gelatin by incubation for 1 hour at room temperature. Fluorescent tagged JY-8 cells (a human EBV-transformed B cell line expressing LFA-1 on its surface; 50 µL at $2 \times 10^6$ cells/ml in RPMI 1640 (standard cell culture medium)/1% fetal bovine serum) are added to the wells. For fluorescent labeling of JY-8 cells, $5 \times 10^6$ cells washed once in RPMI 1640 are resuspended in 1 mL of RPMI 1640 containing 2 µM Calceiun AM (MolecularProbes), are incubated at 37° C for 30 minutes and washed once with RPMI-1640/1% fetal bovine serum. Dilutions of compounds to be assayed for ICAM-1/LFA-1 antagonistic activity are prepared in RPMI-1640/1% fetal bovine serum from 10 mM stock solutions in DMSO and 50 µL are added to duplicate wells. Microtiter plates are incubated for 45 minutes at room temperature and the wells are washed gently once with RPMI-1640/1% fetal bovine serum. Fluorescent intensity is measured in a fluorescent plate reader with an excitation wavelength at 485 nM and an emission wavelength at 530 nM. The percent inhibition of a candidate compound at a given concentration is calculated using the following equation:

$$\% \text{ inhibition} = 100 \times \left\{ 1 - \frac{\text{average OD w/ compound}}{\text{average OD w/o compound}} \right\}$$

and these concentration/inhibition data are used to generate dose response curves, from which $IC_{50}$ values are derived. Compounds of the present invention exhibit blocking activity in the above assay as illustrated in Table 2.

TABLE 2

| Compound of Example | % inhibition @ 4 µM |
|---|---|
| 3 | 90% @ 2 µM |
| 7 | 84% @ 1 µM |
| 8 | 70% @ 4 µM |
| 9 | 76% @ 4 µM |
| 10 | 72% @ 4 µM |
| 13 | 86% @ 1 µM |
| 14 | 80% @ 1 µM |
| 16 | 88% @ 2 µM |
| 17 | 86% @ 2 µM |
| 18 | 84% @ 2 µM |
| 21 | 88% @ 2 µM |
| 22 | 92% @ 2 µM |
| 28 | 90% @ 2 µM |
| 30 | 89% @ 2 µM |
| 31 | 88% @ 2 µM |
| 32 | 86% @ 2 µM |

The ability of the compounds of this invention to treat arthritis can be demonstrated in a murine collagen-induced arthritis model according to the method of Kakimoto, et al., *Cell Immunol* 142: 326–337, 1992, in a rat collagen-induced arthritis model according to the method of Knoerzer, et al., *Toxicol Pathol* 25:13–19, 1997, in a rat adjuvant arthritis model according to the method of Halloran, et al., *Arthritis Rheum* 39: 810–819, 1996, in a rat streptococcal cell wall-induced arthritis model according to the method of Schimmer, et al., *J Immunol* 160: 1466–1477, 1998, or in a SCID-mouse human rheumatoid arthritis model according to the method of Oppenheimer-Marks et al., *J Clin Invest* 10 1: 1261–1272, 1998

The ability of the compounds of this invention to treat Lyme arthritis can be demonstrated according to the method of Gross et al., *Science* 281, 703–706, 1998.

The ability of compounds of this invention to treat Lyme arthritis can be demonstrated in a murine allergic asthma model according to the method of Wegner et al., *Science* 247:456–459, 1990, or in a murine non-allergic asthma model according to the method of Bloemen et al., *Am J Respir Crit Care Med* 153:521–529, 1996.

The ability of compounds of this invention to treat inflammatory lung injury can be demonstrated in a murine oxygen-induced lung injury model according to the method of Wegner et al., *Lung* 170:267–279, 1992, in a murine immune complex-induced lung injury model according to the method of Mulligan et al., *J Immunol* 154:1350–1363, 1995, or in a murine acid-induced lung injury model according to the method of Nagase, et al., *Am J Respir Crit Care Med* 154:504–510, 1996.

The ability of compounds of this invention to treat inflammatory bowel disease can be demonstrated in a rabbit chemical-induced colitis model according to the method of Bennet et al., *J Pharmacol Exp Ther* 280:988–1000, 1997.

The ability of compounds of this invention to treat autoimmune diabetes can be demonstrated in an NOD mouse model according to the method of Hasagawa et al., *Int Immunol* 6:831–838, 1994, or in a murine streptozotocin-induced diabetes model according to the method of Herrold et al., *Cell Immunol* 157:489–500, 1994.

The ability of compounds of this invention to treat inflammatory liver injury can be demonstrated in a murine liver injury model according to the method of Tanaka et al., *J Immunol* 151:5088–5095, 1993.

The ability of compounds of this invention to treat inflammatory glomerular injury can be demonstrated in a rat nephrotoxic serum nephritis model according to the method of Kawasaki, et al., *J Immunol* 150:1074–1083, 1993.

The ability of compounds of this invention to treat radiation-induced enteritis can be demonstrated in a rat abdominal irradiation model according to the method of Panes et al., *Gastroenterology* 108:1761–1769, 1995.

The ability of compounds of this invention to treat radiation pneumonitis can be demonstrated in a murine pulmonary irradiation model according to the method of Hallahan et al., *Proc Natl Acad Sci U S A* 94:6432–6437, 1997.

The ability of compounds of this invention to treat reperfusion injury can be demonstrated in the isolated rat heart according to the method of Tamiya et al., *Immunopharmacology* 29(1): 53–63, 1995, or in the anesthetized dog according to the model of Hartman et al., *Cardiovasc Res* 30(1): 47–54, 1995.

The ability of compounds of this invention to treat pulmonary reperfusion injury can be demonstrated in a rat lung allograft reperfusion injury model according to the method of DeMeester et al., *Transplantation* 62(10): 1477–1485, 1996, or in a rabbit pulmonary edema model according to the method of Horgan et al., *Am J Physiol* 261(5): H1578-H1584, 1991.

The ability of compounds of this invention to treat stroke can be demonstrated in a rabbit cerebral embolism stroke model according the method of Bowes et al., *Exp Neurol* 119(2): 215–219, 1993, in a rat middle cerebral artery ischemia-reperfusion model according to the method of Chopp et al., *Stroke* 25(4): 869–875, 1994, or in a rabbit reversible spinal cord ischemia model according to the method of Clark et al., *Neurosurg* 75(4): 623–627, 1991.

The ability of compounds of this invention to treat peripheral artery occlusion can be demonstrated in a rat skeletal muscle ischemia/reperfusion model according to the method of Gute et al., *Mol Cell Biochem* 179: 169–187. 1998.

The ability of compounds of this invention to treat graft rejection can be demonstrated in a murine cardiac allograft rejection model according to the method of Isobe et al., *Science* 255: 1125–1127, 1992, in a murine thyroid gland kidney capsule model according to the method of Talento et al., *Transplantation* 55: 418–422, 1993, in a cynomolgus monkey renal allograft model according to the method of Cosimi et al., *J Immunol* 144: 4604–4612, 1990, in a rat nerve allograft model according to the method of Nakao et al., *Muscle Nerve* 18: 93–102, 1995, in a murine skin allograft model according to the method of Gorczynski and Wojcik, *J Immunol* 152 : 2011–2019, 1994, in a murine corneal allograft model according to the method of He et al., *Opthalmol Vis Sci* 35: 3218–3225, 1994, or in a xenogeneic pancreatic islet cell transplantation model according to the method of Zeng et al., Transplantation 58:681–689, 1994.

The ability of compounds of this invention to treat graft-vs.-host disease (GVHD) can be demonstrated in a murine lethal GVHD model according to the method of Haming et al., *Transplantation* 52:842–845, 1991.

The ability of compounds of this invention to treat cancers can be demonstrated in a human lymphoma metastasis model (in mice) according to the method of Aoudjit et al., *J Immunol* 161:2333–2338, 1998.

All references cited are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims:

We claim:

1. A compound of the structure

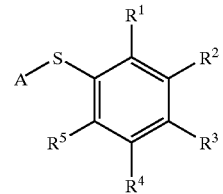

or a pharmaceutically-acceptable salt, optical isomer or prodrug thereof, wherein $R^1$, $R^2$, $R^3$, $R^4$ and $R^5$ are each independently selected from the group consisting of hydrogen, halogen, alkyl, haloalkyl, alkoxy, cyano, nitro, cycloalkyl, carboxaldehyde, "cis-cyclopropanoic acid", "trans-cyclopropanoic acid", "cis-cyclopropanamide", and "trans-cyclopropanamide", wherein "cis-cyclopropanoic acid", and "trans-cyclopropanoic acid" are defined as

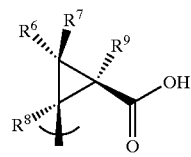

"cis-cyclopropanoic acid"

-continued

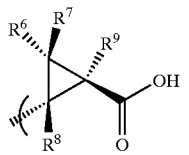

"trans-cyclopropanoic acid", and

"cis-cyclopropanamide", and "trans-cyclopropanamide" are defined as

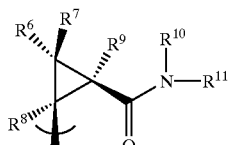

"cis-cyclopropanamide"

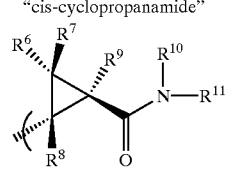

"trans-cyclopropanamide";

wherein
$R^6$ and $R^7$ are each independently selected from the group consisting of hydrogen, alkyl, carboxy, hydroxyalkyl and carboxyalkyl;

$R^8$ and $R^9$ are each independently selected from the group consisting of hydrogen, alkyl, carboxyalkyl, alkylaminocarbonylalkyl and dialkylaminocarbonylalkyl;

and $R^{10}$ and $R^{11}$ are each independently selected from the group consisting of hydrogen, alkyl, cycloalkyl, alkoxycarbonylalkyl, carboxyalkyl, hydroxyalkyl, heterocyclyl, heterocyclylalkyl and heterocyclylamino, or $R^{10}$ and $R^{11}$ are taken together with N to form a three to seven membered unsubstituted heterocyclyl or substituted heterocyclyl ring, substituted with one or more than one substituents $R^{15}$, each substituent $R^{15}$ independently selected from the group consisting of alkyl, alkoxy, alkoxyalkyl, cycloalkyl, aryl, heterocyclyl, heterocyclylcarbonyl, heterocyclylalkylaminocarbonyl, hydroxy, hydroxyalkyl, hydroxyalkoxyalkyl, carboxy, carboxyalkyl, carboxycarbonyl, carboxaldehyde, alkoxycarbonyl, arylalkoxycarbonyl, aminoalkyl, aminoalkanoyl, carboxamido, alkoxycarbonylalkyl, carboxamidoalkyl, cyano, tetrazolyl, alkanoyl, hydroxyalkanoyl, alkanoyloxy, alkanoylamino, alkanoyloxyalkyl, alkanoylaminoalkyl, sulfonate, alkylsulfonyl, alkylsulfonylaminocarbonyl, arylsulfonylaminocarbonyl and heterocyclylsulfonylaminocarbonyl;

and wherein A is an unsubstituted aryl or unsubstituted heterocyclyl group, or a substituted aryl or substituted heterocyclyl group, substituted with one or more than one substituents $R^{12}$, wherein $R^{12}$ is selected from the group consisting of halogen, alkyl, aryl, haloalkyl, hydroxy, alkoxy, alkoxyalkyl, alkoxycarbonyl, alkoxyalkoxy, hydroxyalkyl, aminoalkyl, aminocarbonyl, alkyl(alkoxycarbonylalkyl) aminoalkyl, heterocyclyl, heterocyclylalkyl, carboxaldehyde, carboxaldehyde hydrazone, carboxamide, alkoxycarbonylalkyl, carboxy, carboxyalkyl, cycloalkoxy, carboxythioalkoxy, carboxycycloalkoxy, thioalkoxy, carboxyalkylamino, trans-cinnamyl, carboxyalkoxy, hydroxyalkylaminocarbonyl, cyano, amino, heterocyclylalkylamino, and heterocyclylalkylaminocarbonyl;

and wherein $R^1$, $R^2$, $R_3$, $R^4$, $R^5$, $R^6$, $R^7$, $R^8$, $R^9$, $R^{10}$, $R^{11}$, $R^{12}$ and $R^{15}$ are unsubstituted or substituted with at least one electron donating or electron withdrawing group, subject to the proviso that one or more than one of $R^1$ or $R^3$ is selected from the group consisting of "cis-cyclopropanoic acid", "trans-cyclopropanoic acid", "cis-cyclopropanamide", and "trans-cyclopropanamide" as defined above.

2. A compound according to claim 1 wherein $R^3$ is "cis-cyclopropanamide" or "trans-cyclopropanamide";

$R^1$ and $R^2$ are each independently selected from the group consisting of hydrogen, halogen, haloalkyl and nitro; and $R^4$ and $R^5$ are each independently selected from the group of hydrogen and alkyl.

3. A compound according to claim 1 of the structure

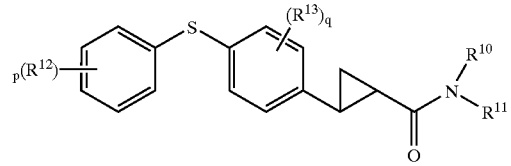

wherein
p is an integer of one to five;
q is an integer of one to four;
$R^{12}$ and $R^{13}$, at each occurrence, are independently selected from the group consisting of hydrogen, halogen, alkyl, haloalkyl, alkoxy, carboxyalkoxy, carboxyalkyl and heterocyclyl;

$R^{10}$ and $R^{11}$ are each independently selected from the group consisting of hydrogen, alkyl, cycloalkyl, alkoxycarbonylalkyl, carboxyalkyl, hydroxyalkyl, heterocyclyl, heterocyclylalkyl and heterocyclylamino, or $R^{10}$ and $R^{11}$ are taken together N to form a three to seven membered unsubstituted heterocyclyl or substituted heterocyclyl ring, substituted with one or more than one substituents $R^{15}$, each substituent $R^{15}$ independently selected from the group consisting of alkyl, alkoxy, alkoxyalkyl, cycloalkyl, aryl, heterocyclyl, heterocyclylcarbonyl, heterocyclylalkylaminocarbonyl, hydroxy, hydroxyalkyl, hydroxyalkoxyalkyl, carboxy, carboxyalkyl, carboxycarbonyl, carboxaldehyde, alkoxycarbonyl, arylalkoxycarbonyl, aminoalkyl, aminoalkanoyl, carboxamido, alkoxycarbonylalkyl, carboxamidoalkyl, cyano, tetrazolyl, alkanoyl, hydroxyalkanoyl, alkanoyloxy, alkanoylamino, alkanoyloxyalkyl, alkanoylaminoalkyl, sulfonate, alkylsulfonyl, alkylsulfonylaminocarbonyl, arylsulfonylaminocarbonyl and heterocyclylsulfonylaminocarbonyl;

and wherein $R_{10}$, $R^{11}$, $R^{12}$, $R^{13}$ and $R^{15}$ are unsubstituted or substituted with at least one electron donating or electron withdrawing group.

4. A compound according to claim 3 wherein $R^{10}$ and $R^{11}$ are taken together with N to form a three to seven membered unsubstituted heterocyclyl or substituted heterocyclyl ring; said ring selected from the group consisting of piperidine, morpholine, piperazine, pyrrolidine and azetidine;

p is one;

q is one or two;

$R^{13}$, at each occurence is selected from the group consisting of halogen and haloalkyl; and $R^{12}$ is selected from the group consisting of halogen, alkyl, alkoxy, carboxyalkoxy, carboxyalkyl, and heterocyclyl.

5. A compound according to claim 1 of the structure

[Chemical structure shown]

wherein the circle Q represents a three to seven membered heterocyclyl ring;

the circle T represents a five to seven membered heterocyclyl ring;

r is an integer of one to three;

s is an integer of one to five;

n is an integer of one to four;

$R^1$ and $R^2$, are each independently selected from the group consisting of hydrogen, halogen and haloalkyl;

$R^{14}$ and $R^{15}$, at each occurrence, are independently selected from the group consisting of hydrogen, halogen, alkyl, alkoxy and carboxy; and wherein $R^1$, $R^2$, $R^{14}$ and $R^{15}$ are unsubstituted or substituted with at least one electron donating or electron withdrawing group.

6. A compound according to claim 5 wherein circle T represents pyrrolidine, n is three; and circle Q represents a three to seven membered heterocyclic ring selected from the group consisting of piperidine and morpholine.

7. A compound according to claim 1 selected from the group consisting of (±)-2-bromophenyl)[2-trifluoromethyl-4-(trans-(2-((3-(-pyrrolidin-2-onyl)-prop-1-ylamino)carbonyl)cycloprop-1-yl)phenyl]sulfide, (±)-2-isopropylphenyl[2,3-dichloro4-(trans-(carboxymethylamino)carbonyl)cycloprop-1-yl)phenyl] sulfide, (±)-(2-isopropylphenyl)[2,3-dichloro-4-(trans-(2-(3-carboxypiperidine))carbonyl)cycloprop-1-yl)phenyl) sulfide, (±)-(2-(2-carboxyethyl)phenyl)[2-trifluoromethyl-4-(trans-(2-((3-(1-pyrrolidin-2-onyl)-prop-1-ylamino) carbonyl)cycloprop-1-yl)phenyl]sulfide, (±)-(2-morpholin-1-ylphenyl)[2-trifluoromethyl-4-(trans-2-((3-(1-pyrrolidin-2-onyl)-prop-1-ylamino)carbonyl)cycloprop-1-yl)phenyl] sulfide, (±)-2-morpholin-1-ylphenyl[2-chloro-4-(trans-(2-((3-(1-pyrrolidin-2-onyl)-prop-1-ylamino)carbonyl) cycloprop-1-yl)phenyl]sulfide, (±)-(2-piperidin-1-ylphenyl) [2-trifluoromethyl-4-(trans-(2-((3-(1-pyrrolidin-2-onyl)-prop-1-ylamino)carbonyl)cycloprop-1-yl)phenyl]sulfide, (±)-(2-pyrrolidin-1-ylphenyl)[(2-trifluoromethyl-4-(trans-(2-((3-(1-pyrrolidin-2-onyl)-prop-1-ylamino(carbonyl) cycloprop-1-yl)phenyl]sulfide, (±)-(3-morpholin-1-ylphenyl)[2-trifluoromethyl-4-(trans-(2-((3-(1-pyrrolidin-2-onyl)-prop-1-ylamino)carbonyl)cycloprop-1-yl)phenyl] sulfide, (±)-(2-morpholin-1-ylphenyl)[2,3-dichloro-4-(trans-(2-carboxycycloprop-1-yl)phenyl]sulfide, (±)-(2-morpholin-1-ylphenyl)[2-trifluoromethyl-4-(transi-(2-((3-(1-pyrrolidin-2-onyl)-propyl-N-methylamino)cabonyl) cycloprop-1-yl)phenyl]sulfide, (±)-(2-bromophenyl)[2,3-dichloro-4-(trans-(2-((3-(1-pyrrolidin-2-onyl)-prop-1-ylamino)carbonyl)cycloprop-1-yl)phenyl]sulfide, (±)-(2-isopropylphenyl)[2,3-dichloro-4-(trans(2-(2-carboxyethylamino)carbonyl)cycloprop-1-yl)phenyl] sulfide, (±)-(2-isopropylphenyl)[2,3dichloro-4(trans-(2-(2carboxypropyl amino)carbonyl)cycloprop-1-yl)phenyl] sulfide, (±)-2-isopropylphenyl)[2,3-dichloro-4-(trans-(2-(3-carboxypropyl amino)carbonyl)cycloprop-1-yl)phenyl] sulfide, (±)-(2-isopropylphenyl)[2,3-dichloro-4-(trans-(2-(4-carboxypiperidin-1-yl)carbonyl)cycloprop-1-yl)phenyl] sulfide, (±)-(2-isopropylphenyl)[2,3-dichloro-4-(trans-(2-(2-carboxypiperidin-1-yl)carbonyl)cycloprop-1-yl)phenyl] sulfide, (±)-(2-isopropylphenyl)[2,3-dichloro-4-(trans-(2-(2-(morpholin-1-yl)carbonyl)cycloprop-1-yl)phenyl] sulfide, (±)-(2-isopropylphenyl)[2,3-dichloro-4-(trans-(2-(4-acetylpiperazin-1-yl)carbonyl)cycloprop-1-yl)phenyl] sulfide, (±)-(2-isopropylphenyl)[2,3-dichloro-4-(trans-(2-((3-(1-pyrrolidin-2-onyl)-prop-1-ylamino)carbonyl) cycloprop-1-yl)phenyl]sulfide, (±)-(2-isopropylphenyl)[2,3-dichloro-4-(trans-(2-(pyrrolidin-1-yl)carbonyl)cycloprop-1-yl)phenyl]sulfide, (±)-(2-isopropylphenyl)[2,3-dichloro-4-(trans-2-(cyclobutylaminocarbonyl)cycloprop-1-yl)phenyl] sulfide, (±)-(2-isopropylphenyl)[2,3-dichloro-4-(trans-(2-(azetidin-1-yl)carbonyl)cycloprop-1-yl)phenyl]sulfide, (±)-(2-isopropylphenyl)[2,3-dichloro-4-(trans-(2-(2-morpholin-1-ylethyl)carbonyl)cycloprop-1-yl)phenyl]sulfide, (2-(3-carboxypiperidin-1-yl)phenyl)[2-trifluoromethyl-4-(trans-(2-((3-(1-pyrrolidin-2-onyl)-prop-1-ylamino)carbonyl) cycloprop-1-yl)phenyl]sulfide, (2-(morpholin-1-yl)phenyl) [2-trifluoromethyl-4-(trans-(2-((3-(1-pyrrolidin-2-onyl)-prop-1-ylamino)carbonyl)cycloprop-1-yl)phenyl]sulfide, (2-(3-carboxypiperidin-1-yl)phenyl)[2,3-dichloro-4-(trans-(2-((3-(1-pyrrolidin-2-onyl)prop-1-ylamino-carbonyl) cycloprop-1-yl)phenyl]sulfide(2-methoxophenyl)[2,3-dichloro-4-(trans-2-(carboxymethylamino)carbonyl) cycloprop-1-yl)phenyl]sulfide, (2-methoxyphenyl)[2,3-dichloro-4-(trans-2-(2-(3-carboxypropylamino)carbonyl) cycloprop-1-yl)phenyl]sulfide, (2-methoxyphenyl)[2,3-dichloro-4-(trans-2-(4-carboxypiperidin-1-yl)carbonyl) cycloprop-1-yl)phenyl]sulfide, (2-methoxyphenyl)[2,3-dichloro-4-(trans-2-(3-carboxypiperidin-1-yl)carbonyl) cycloprop-1-yl)phenyl]sulfide, (2-methoxyphenyl)[2,3-dichloro-4-(trans-2-(2-carboxypiperidin-1-yl)carbonyl) cycloprop-1-yl)phenyl]sulfide, (2-methoxyphenyl)[2,3-dichloro-4-(trans-2-(2-carboxyethylamino)carbonyl) cycloprop-1-yl)phenyl]sulfide, (2-methoxophenyl)[2,3-dichloro-4-(trans-2-(2-carboxyethylamino)carbonyl cycloprop-1-yl)phenyl]sulfide, (2-methoxyphenyl)[2,3-dichloro-4-(trans-2-(3-carboxypropylamino)carbonyl) cycloprop-1-yl)phenyl]sulfide, (2-methoxyphenyl)(2,3-dichloro-4-(trans-2-(4-carboxypiperidin-1-yl)carbonyl) cycloprop-1-yl)phenyl]sulfide, (2-methoxyphenyl)[2,3-dichloro-4-(trans-2-(3-carboxypiperidin-1-yl)carbonyl) cycloprop-1-yl)phenyl]sulfide and (2-methoxyphenyl)[2,3-dichloro-4-(trans-2-((3-carboxypiperidin-1-ylcarbonyl) cycloprop-1-yl)phenyl]sulfide, and (2-methoxyphenyl[2,3-dichloro-4-(trans-(2-((3-(1-pyrrolidin-2-onyl)-prop-1-ylamino)carbonyl)cycloprop-1-yl)phenyl]sulfide.

8. A composition comprising:

a compound according to claim 1 and a pharmaceutically acceptable carrier.

9. A method of inhibiting inflamation or suppressing immune response in a mammal comprising administering to said mammal a therapeutic amount of a compound according to claim 1.

* * * * *

UNITED STATES PATENT AND TRADEMARK OFFICE
CERTIFICATE OF CORRECTION

PATENT NO.      : 6,521,619 B2                                         Page 1 of 2
DATED           : February 18, 2003
INVENTOR(S)     : James T. Link and Bryan K. Sorensen It is certified that error appears in the above-identified patent and that said Letters Patent is hereby corrected as shown below:

Title page,
Item [73], Assignee, "Icos" should read -- ICOS --.

Column 50,
Line 10, "$R_3$," should read -- $R^3$, --.
Line 47, after "taken together", insert -- with --.
Line 65, "$R_{10}$," should read -- $R^{10}$, --.

Column 51,
Line 9, "occurence" should read -- occurrence --.
Lines 54-56, "(±)-2-bromophenyl)[2-trifluoromethyl-4-(trans-(2-((3-(-pyrrolidin-2-onyl)-prop-1-ylamino)carbonyl)cycloprop-1-yl)phenyl]sulfide," should read
-- (±)-2-bromophenyl)[2-trifluoromethyl-4-(trans-(2-((3-(1-pyrrolidin-2-onyl)-prop-1-ylamino)carbonyl)cycloprop-1-yl)phenyl]sulfide, --.
Lines 56-59, "(±)-2-isopropylphenyl[2,3-dichloro4-(trans-(carboxymethylamino)carbonyl)cycloprop-1-yl)phenyl]sulfide," should read -- (±)-2-isopropylphenyl[2,3-dichloro-4-(trans-(carboxymethylamino)carbonyl)cycloprop-1-yl)phenyl]sulfide, --.
Lines 59-61, "(±)-(2-isopropylphenyl)[2,3-dichloro-4-(trans-(2-(3-carboxypiperidine))carbonyl)cycloprop-1-yl)phenyl)sulfide," should read -- (±)-(2-isopropylphenyl)[2,3-dichloro-4-(trans-(2-(3-carboxypiperidine))carbonyl)cycloprop-1-yl)phenyl]sulfide, --.

Column 52,
Lines 12-15, "(±)-(2-morpholin-1-ylphenyl)[2-trifluoromethyl-4-(transi-(2-((3-1-pyrrolidin-2-onyl)-propyl-N-methylamino)cabonyl)cycloprop-1-yl)phenyl]sulfide," should read -- (±)-(2-morpholin-1-ylphenyl)[2-trifluoromethyl-4-(transi-(2((3-(1-pyrrolidin-2-onyl)-propyl-N-methylamino)carbonyl)cycloprop-1-yl)phenyl]sulfide, --.
Lines 21-23, "(±)-(2-isopropylphenyl)[2,3dichloro-4(trans-(2-(2carboxypropylamino)carbonyl)cycloprop-1-yl)phenyl]sulfide," should read -- (±)-(2-isopropylphenyl)[2,3-dichloro-4(trans-(2-(2-carboxypropylamino)carbonyl)cycloprop-1-yl)phenyl]sulfide, --.
Lines 50-55, "(2-(3-carboxypiperidin-1-yl)phenyl)[2,3-dichloro-4-(trans-(2-((3-(1-pyrrolidin-2-onyl)prop-1-ylamino-carbonyl)cycloprop-1-yl)phenyl] sulfide(2-methoxophenyl)[2,3-dichloro-4-(trans-2-(carboxymethylamino)carbonyl)cycloprop-1-yl)phenyl]sulfide," should read -- (2-(3-carboxypiperidin-1-yl)phenyl)[2,3-dichloro-4-(trans-(2-((3-(1-pyrrolidin-2-onyl)-prop-1-ylamino-carbonyl)cycloprop-1-yl)phenyl] sulfide(2-methoxophenyl)[2,3-dichloro-4-(trans-2-(carboxymethylamino)carbonyl) cycloprop-1-yl)phenyl]sulfide, --.

UNITED STATES PATENT AND TRADEMARK OFFICE
CERTIFICATE OF CORRECTION

PATENT NO.    : 6,521,619 B2
DATED         : February 18, 2003
INVENTOR(S)   : James T. Link and Bryan K. Sorensen It is certified that error appears in the above-identified patent and that said Letters Patent is hereby corrected as shown below:

Column 53,
Lines 3-5, "(2-methoxyphenyl)(2,3-dichloro-4-(trans-2-(4-carboxypiperidin-1-yl) carbonyl)cycloprop-1-yl)phenyl]sulfide," should read -- (2-methoxyphenyl)[2,3-dichloro-4-(trans-2-(4-carboxypiperidin-1-yl)carbonyl)cycloprop-1-yl)phenyl] sulfide, --.
Lines 7-9, "(2-methoxyphenyl)[2,3-dichloro-4-(trans-2-((3-carboxypiperidin-1-ylcarbonyl)cycloprop-1-yl)phenyl]sulfide," should read -- (2-methoxyphenyl)[2,3-dichloro-4-(trans-2-((3-carboxypiperidin-1-yl)carbonyl)cycloprop-1-yl)phenyl] sulfide,--.

Signed and Sealed this

Twenty-sixth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,521,619 B2         Page 1 of 1
DATED : February 18, 2003
INVENTOR(S) : James T. Link et al.

It is certified that error appears in the above-identified patent and that said Letters Patent is hereby corrected as shown below:

Column 48,
Lines 53, 54 and 66, replace "cis" with the italic word -- cis --.
Lines 54 and 55, replace "trans" with the italic word -- trans --.
Line 57 replace the words "cis" and "trans" with the italic words -- cis and trans --.

Column 49,
Lines 8 and 26, replace "trans" with the italic word -- trans --.
Line 11 replace the words "cis" and "trans" with the italic words -- cis -- and -- trans --.
Line 19 replace "cis" with the italic word -- cis --.

Column 50,
Line 15, replace "cis" with the italic word -- cis --.
Line 16 replace "trans" with the italic word -- trans --.
Lines 17 and 19, replace "the words "cis" and "trans" with the italic words -- cis -- and -- trans --.
Line 18 replace "$R^3$" with -- $R^1$ --.

Column 51,
Lines 55 and 57, replace the word "(trans" with the italic word -- (trans --.
Lines 59, 63, 65 and 67, replace "trans" with the italic word -- trans --.

Column 52,
Lines 3, 5, 8, 11, 12, 17, 19, 25, 27, 29, 32, 34, 37, 39, 40, 42, 45, 48, 51, 54, 56, 58, 60, 62, 65 and 67, replace "trans" with the italic word -- trans --.

Column 53,
Lines 2, 4, 6, 8 and 10, replace "trans" with the italic word -- trans --.

Signed and Sealed this

Seventh Day of October, 2003

JAMES E. ROGAN
*Director of the United States Patent and Trademark Office*